(12) United States Patent
Corver et al.

(10) Patent No.: US 6,946,838 B2
(45) Date of Patent: Sep. 20, 2005

(54) NMR MEASURING SYSTEM

(75) Inventors: Jozef A. W. M. Corver, Nuenen (NL); Paul Stewart, Youngstown, NY (US)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 10/837,108

(22) Filed: Apr. 30, 2004

(65) Prior Publication Data

US 2004/0251904 A1 Dec. 16, 2004

Related U.S. Application Data

(60) Provisional application No. 60/471,125, filed on May 16, 2003.

(51) Int. Cl.$^7$ ................................................. G01V 3/00
(52) U.S. Cl. .................................... 324/307; 324/306
(58) Field of Search ................................ 324/207, 306, 324/309, 311, 303, 318, 307, 300; 177/1

(56) References Cited

U.S. PATENT DOCUMENTS

| | | | |
|---|---|---|---|
| 3,796,873 A | | 3/1974 | Ledgett |
| 4,727,325 A | | 2/1988 | Matsui et al. |
| 5,015,954 A | | 5/1991 | Dechene et al. |
| 5,049,819 A | | 9/1991 | Dechene et al. |
| 5,291,422 A | | 3/1994 | Esztergar |
| 5,302,894 A | | 4/1994 | Hrubes |
| 5,397,987 A | * | 3/1995 | Garritano ................... 324/307 |
| 6,028,428 A | | 2/2000 | Cunningham et al. |
| 6,362,619 B2 | | 3/2002 | Prammer et al. |
| 6,377,049 B1 | | 4/2002 | Benz et al. |
| 6,426,058 B1 | | 7/2002 | Pines et al. |
| 6,479,994 B1 | * | 11/2002 | Hills et al. ................... 324/306 |
| 6,549,007 B1 | * | 4/2003 | Hills et al. ................... 324/306 |
| 6,759,601 B1 | * | 7/2004 | Petty et al. ..................... 177/1 |

FOREIGN PATENT DOCUMENTS

| | | |
|---|---|---|
| DE | 1803372 A1 | 5/1970 |
| GB | 2149509 A | 6/1985 |
| WO | WO 99/67606 A1 | 12/1999 |

OTHER PUBLICATIONS

Derwent WPI Abstract, UNILEVER NV, Package Weight Measuring System, NL 154001B, Jul. 15, 1977 (Corresponds to DE 1803372A1).

* cited by examiner

*Primary Examiner*—Brij B. Shrivastav
(74) *Attorney, Agent, or Firm*—Ira Lee Zebrak; Mary K. Nicholes

(57) ABSTRACT

An improvement in a magnetic resonance method for determining at least one property of multiple samples, including introducing multiple samples into the interrogation zone simultaneously; applying a gradient magnetic field to the interrogation zone wherein different positions within the interrogation zone are sensitive to different specific frequencies; monitoring energy emitted by the samples in the different positions and generating an output signal having a characteristic which is proportional to the energy emitted corresponding thereto in different frequency bands; and, attributing the signals to specific positions and samples, and comparing the output signal characteristics of the specific positions and samples with like data obtained from at least one similar sample to provide an indication of the corresponding property of the samples.

16 Claims, 15 Drawing Sheets

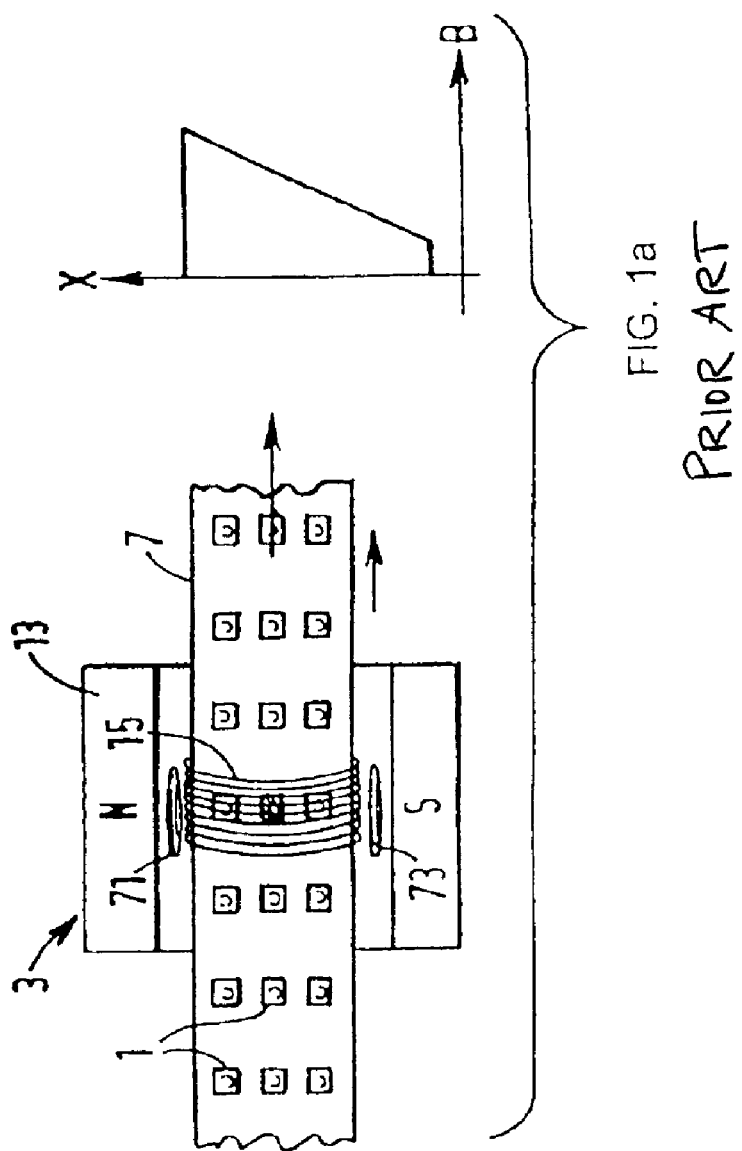

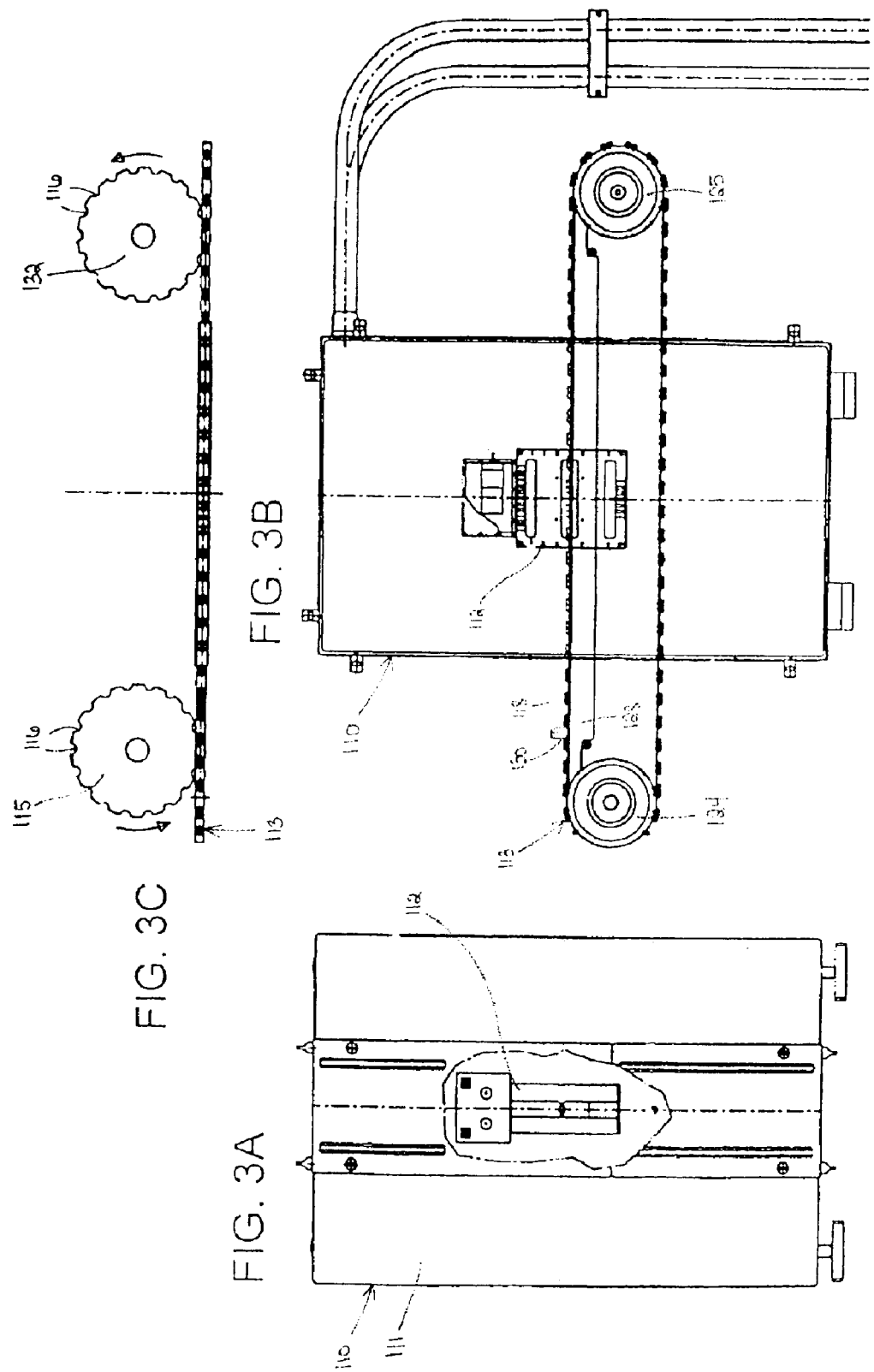

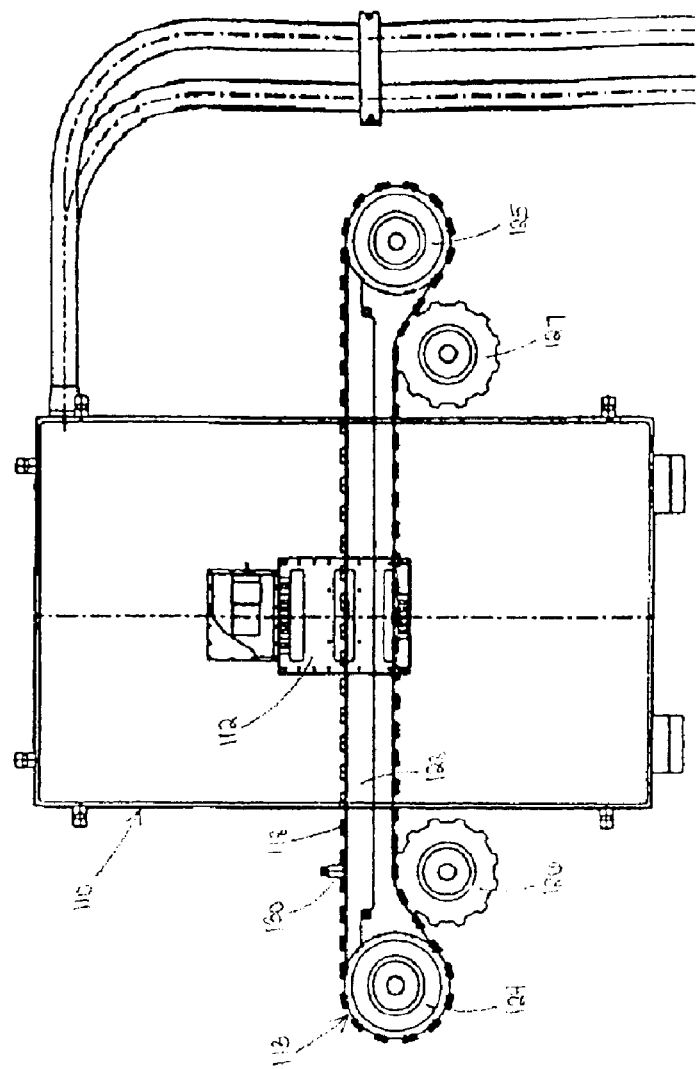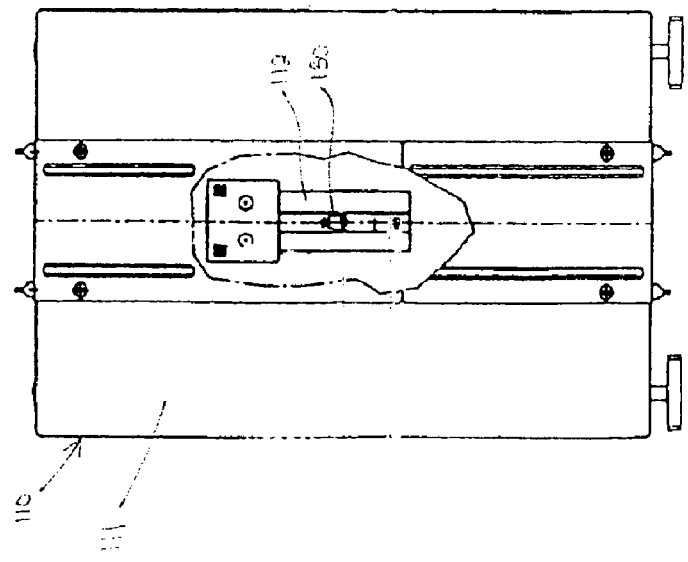

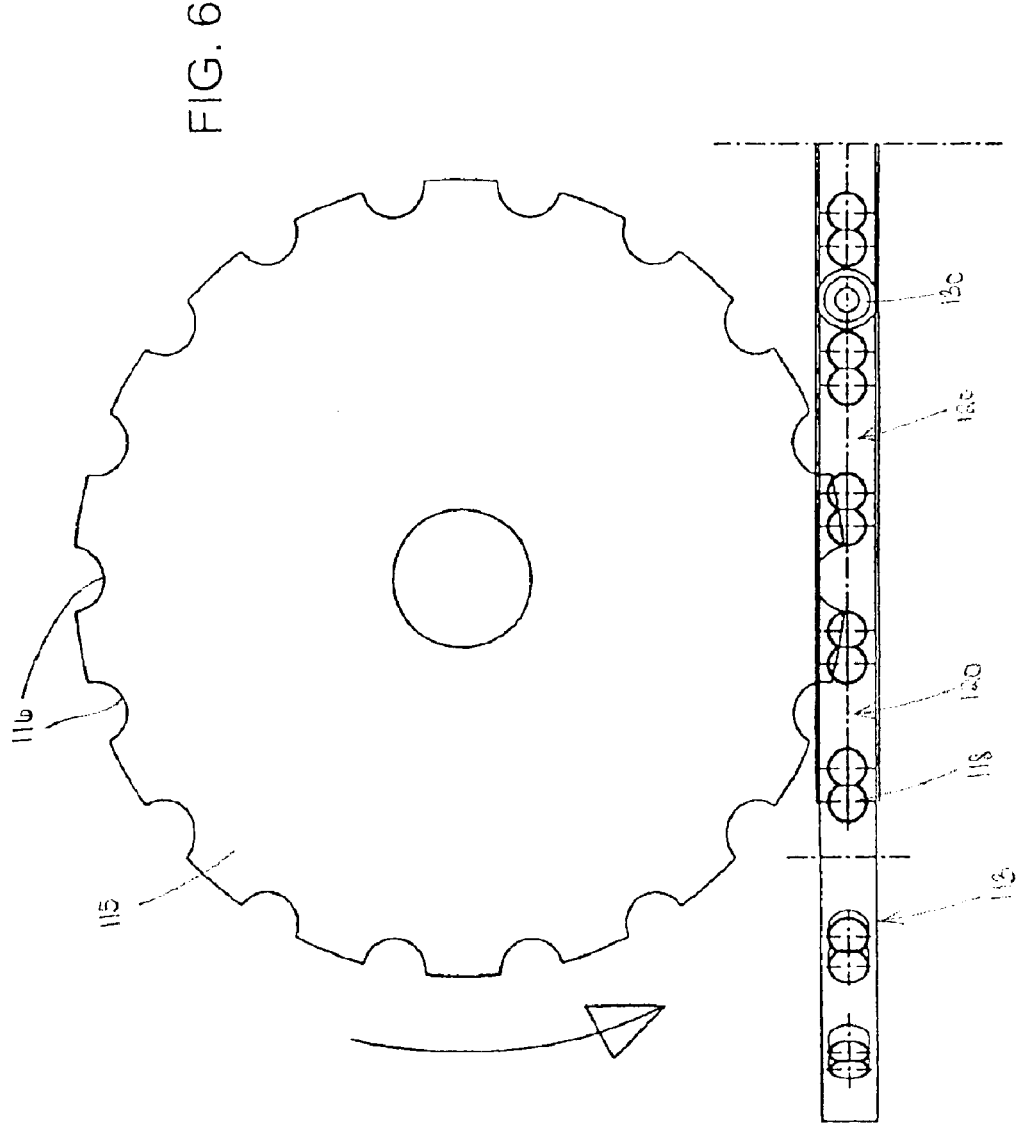

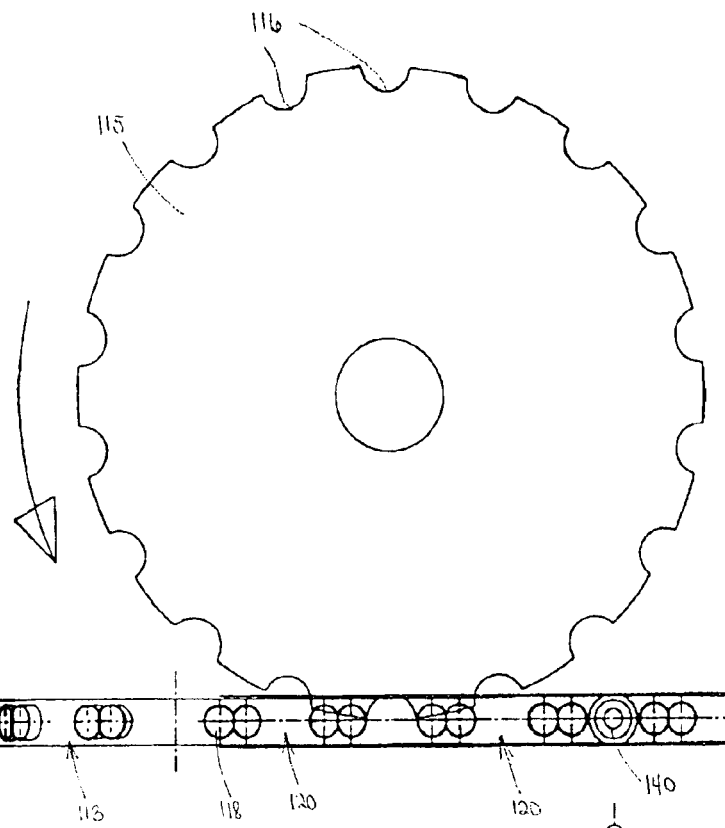
FIG. 7A
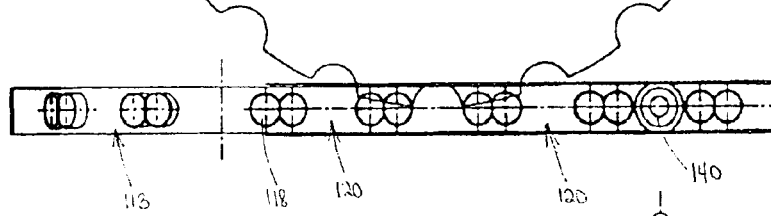
FIG. 7B
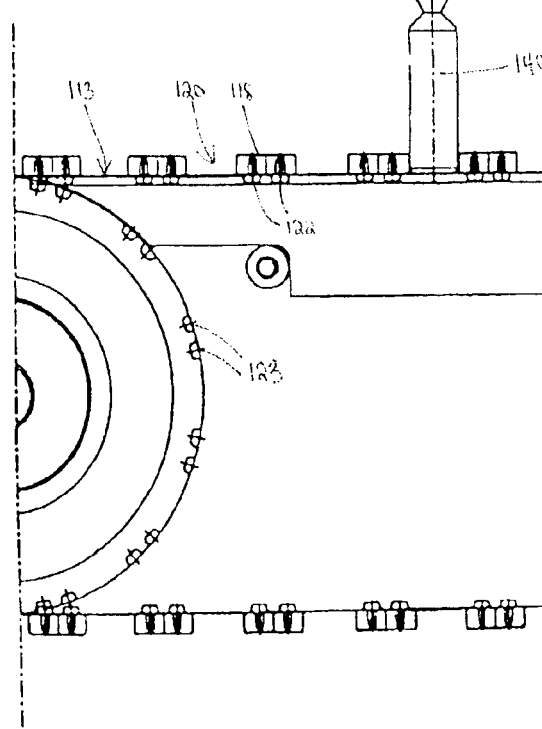
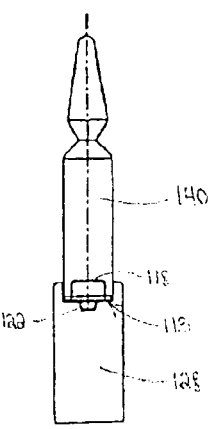
FIG. 7C

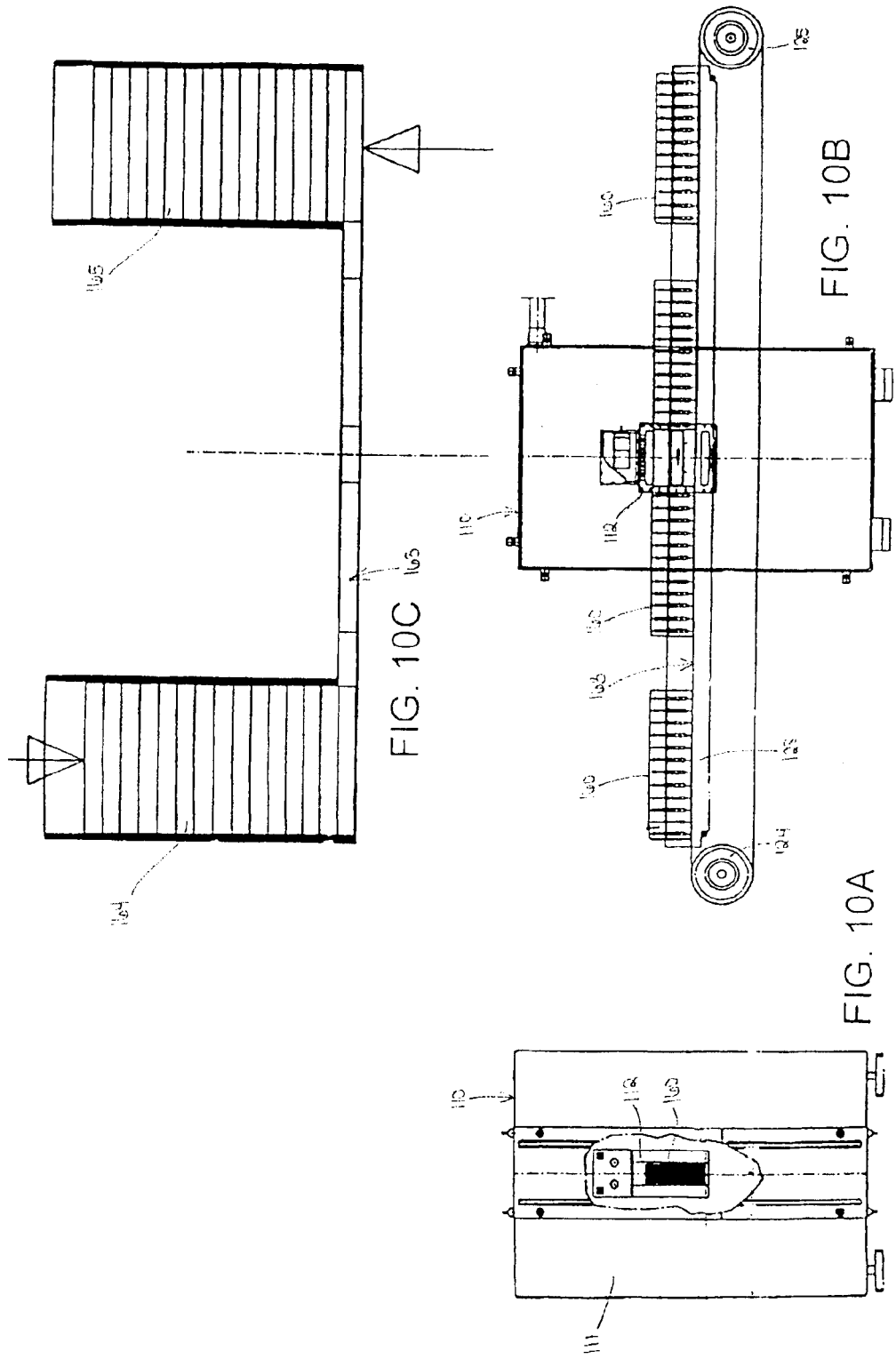

NMR MEASURING SYSTEM

CROSS REFERENCE TO RELATED APPLICATIONS

This application claims the benefit of the filing date of U.S. Provisional Application Ser. No. 60/471,125, filed May 16, 2003, which is incorporated herein by reference.

FIELD OF THE INVENTION

The invention relates to non-contact check weighing of samples using NMR techniques.

BACKGROUND

The nuclei of atoms that have a magnetic moment will have sharply defined frequencies of nuclear oscillation in a strong magnetic field (Larmor frequency). The frequency of oscillation of each atomic nucleus will depend on its mass, its dipole moment, the chemical bonding of the atom, the atom's environment (which will be affected by electromagnetic coupling to other atoms in the vicinity), and the strength of the magnetic field seen by the atom. Thus, the frequency of oscillation will be characteristic, not only of the various atomic species, but also of their molecular environments. By resonantly exciting these oscillations, the atomic species and their environments can be determined with accuracy. This phenomenon is known as "nuclear magnetic resonance," or NMR.

If a pulse of RF energy is applied at a resonance frequency of atoms of a particular species and environment (e.g. hydrogen atoms in a water environment), the atomic nuclei of this type and environment will resonantly be excited, and will later make a transition back to a low state of excitation. This transition is accompanied by emission of a radio-frequency signal, at the excitation frequency or a known lower frequency. The signal is known as the Free Induction Decay (FID) The amplitude and the shape of this FID-curve is related to the amount of nuclei involved in the process and to specific conditions and properties of the atoms in relation to the environment.

The use of NMR techniques in measurement, detection and imaging has become desirable in many scientific fields of endeavor. The non-invasive, non-destructive nature of NMR has facilitated application to industrial instrumentation, analysis and control tasks.

Almost every element in the periodic table has an isotope with a non-zero nuclear spin. This spin causes the nuclei to be magnetically active. Among magnetically active nuclei, NMR can only be performed on isotopes whose natural abundance is high enough to be detected. Commonly encountered magnetically active nuclei are $^1H$, $^{13}C$, $^{19}F$, $^{23}Na$, and $^{31}P$. The most common is $^1H$, which also possesses the largest magnetic moment, rendering it most advantageous for the performance of NMR spectroscopy.

Upon application to a sample of a static magnetic field, $B_o$, sample nuclear spins align with the field, parallel to the direction of the field. The magnetic moments can align themselves either parallel (NSNS) or antiparallel (NNSS) to the static field. Alignment parallel to the static field is the lower energy state and alignment against the field is the higher energy state. At room temperature, the number of nuclei having spins in the lower energy level, $N^+$, slightly outnumbers the number in the upper level, $N^-$. Boltzmann statistics provides that $$N^-/N^+ = \exp(-E/kT), \quad (1)$$

where E is the energy difference between the spin states; k is Boltzmann's constant, $1.3805 \times 10^{-23}$ J/Kelvin; and T is the temperature in Kelvin. As the temperature decreases, so does the ratio $N^-/N^+$. As the temperature increases, the ratio approaches unity.

Owing to the slight imbalance of nuclei having spins at the higher state, a sample in a static magnetic field will exhibit a magnetization parallel to the static field. Magnetization results from nuclear precession (relaxation) around the static magnetic field. The frequency of this precession depends on the strength of the static magnetic field, and is defined as:

$$\nu = \gamma B, \quad (2)$$

where B is the magnetic field strength and Gamma is the gyromagnetic ratio of at least one atom, typically hydrogen, in the sample material. The gyromagnetic ratio is related to the magnetic moment of the nucleus under analysis. The gyromagnetic ratio of protons is 42.57 MHz/Tesla. The frequency thus measured is known as the Larmor frequency, $\nu$, which can be conceptualized as the rate of precession of the nucleus in the static magnetic field or the frequency corresponding to the energy at which a transition between the upper and lower states can take place.

The fundamental NMR signal is derived by inducing transitions between these different alignments. Such transitions can be induced by exposing a sample to the magnetic component of an RF (radio frequency) signal, typically generated by an RF coil. When the magnetic component is applied perpendicularly to the magnetic field a resonance occurs at a particular RF frequency (identical to the precession frequency, the Larmor frequency), corresponding to the energy emitted or absorbed during a transition between the different alignments. When a strong magnetic field, such as in the range of 0.1–2 Tesla (1 T=10,000 Gauss) is used, this resonance typically occurs in the megahertz frequency range, corresponding to FM radio. Hence the radiation is known as Radio Frequency (RF) radiation.

The signal in NMR spectroscopy results from the difference between the energy absorbed by the spins which make a transition from the lower energy state to the higher energy state, and the energy emitted by the spins which simultaneously make a transition from the higher energy state to the lower energy state. The signal is thus proportional to the population difference between the states. NMR spectroscopy gains its high level of sensitivity since it is capable of detecting these very small population differences. It is the resonance, or exchange of energy at a specific frequency between the spins and the spectrometer, which gives NMR its sensitivity.

Pulsed NMR spectroscopy is a technique involving a magnetic burst or pulse, which is designed to excite the nuclei of a particular nuclear species of a sample being measured after the protons of such sample have first been brought into phase in an essentially static magnetic field; in other words the precession is modified by the pulse. Typically, the direction of the static magnetic field, $B_o$, is thought of as being along the Z-axis in three-dimensional space. At equilibrium, the net magnetization vector lies along the direction of the applied magnetic field $B_o$ and is called the equilibrium magnetization $M_0$. In this configuration, the Z component of magnetization $M_z$ equals $M_o$. $M_z$ is referred to as the longitudinal magnetization. There is no transverse ($M_x$ or $M_y$) magnetization in such a case.

It is possible to change the net magnetization by exposing the nuclear spin system to energy of a frequency equal to the energy difference between the spin states. If enough energy is put into the system, it is possible to saturate the spin system and make $M_z=0$. The time constant, which describes how $M_z$ returns to its equilibrium value, is called the spin lattice relaxation time ($T_1$). The equation governing this behavior as a function of the time t after its displacement is:

$$M_z = M_0(1 - e^{-t/T1}) \quad (3)$$

$T_1$ is therefore defined as the time required to change the Z component of magnetization by a factor of e. Hence, at $t=T_1$, $M_z=0.63\ M_0$. In order to properly perform repeated measurements, which is necessary in order to reduce background noise and enhance signal quality, $M_0$ should be allowed to return to $M_z$. In other words, the longitudinal magnetization $M_z$, which equals zero upon saturation, should be allowed to fully return to the +Z direction and attain its equilibrium value of $M_0$. While this theoretically would take forever, (i.e., following saturation, $M_z=M_0$ when $t=\infty$), it is generally considered sufficient when $M_z=0.99\ M_0$, which occurs when $t=5T_1$. This places time constraints on the speed at which a sample may be measured multiple times or the overall throughput of samples through an interrogation zone.

If the spin system is oversaturated, forcing the net magnetization into the −Z direction, it will gradually return to its equilibrium position along the +Z axis at a rate also governed by $T_1$. The equation governing this behavior as a function of the time t after its displacement is:

$$M_x = M_o (1 - 2e^{-t/T1}) \quad (4)$$

The spin-lattice relaxation time ($T_1$) is the time to reduce the difference between the longitudinal magnetization ($M_z$) and its equilibrium value by a factor of e. Here, too, an elapsed time of $t=5\ T_1$ is required in order for $M_z$ to return to a value of 0.99 $M_O$, placing a similar time constraint on sample throughput.

If the net magnetization is rotated into the XY plane by a 90° pulse, it will rotate about the Z-axis at a frequency equal to the frequency of a photon, having the energy corresponding to a transition between the two energy levels of the spin. This frequency is called the Larmor frequency. In addition to the rotation, the net magnetization, now in the XY plane, starts to dephase because each of the spin packets making it up is experiencing a slightly different magnetic field and hence rotates at its own Larmor frequency. The longer the elapsed time, following the pulse, the greater the phase difference. If the detector coil is sensitive to measurements of fields in the X-direction alone, the dephasing results in a decaying signal, eventually approaching zero. The time constant, which describes this decay of the transverse magnetization, $M_{XY}$, is called the spin-spin relaxation time, $T_2$.

$$M_{XY} = M_{XY0} e^{-t/T2} \quad (5)$$

$T_2$ is always less than or equal to $T_1$. The net magnetization in the XY plane goes to zero while the longitudinal magnetization grows until $M_0$ returns to the +Z direction. Any transverse magnetization behaves the same way.

The spin-spin relaxation time, $T_2$, is the time to reduce the transverse magnetization by a factor of e. The difference between spin-lattice relaxation and spin-spin relaxation is that the former works to return $M_z$ to $M_0$, while the latter works to return $M_{XY}$ to zero. $T_1$ and $T_2$ were discussed separately above, for clarity. That is, the magnetization vectors are considered to fill the XY plane completely before growing back up along the Z-axis. Actually, both processes occur simultaneously, with the only restriction being that $T_2$ is less than or equal to $T_1$.

Two factors contribute to the decay of transverse magnetization—(1) molecular interactions (said to lead to a pure $T_2$ molecular effect), and (2) variations in $B_o$ (the applied static field), said to lead to an inhomogeneous $T_2$ effect. The combination of these two factors is what actually results in the decay of transverse magnetization. The combined time constant is called "$T_2$ star" and is given the symbol $T_2^*$. The relationship between the $T_2$ from molecular processes and that from inhomogeneities in the magnetic field is $$1/T_2^* = 1/T_2 + 1/T_{2inh} \quad (6)$$

The source of the inhomogeneities can be natural fluctuations in a field, or imperfections in the magnets generating the field or magnetic contaminants, such as iron or other ferromagnetic metals.

In practice, to actually measure a sample using NMR, a sample is first placed in a static magnetic field, $B_o$, which is the interrogation zone of the instrument. Next, a magnetic pulse is applied, which rotates the magnetization vector to a desired extent, typically 90° or 180°. A 90° pulse, for example, rotates the magnetization vector from the Z-direction into the XY plane resulting in transverse magnetization, $M_{XY}$, as discussed above. After the application of the pulse, there occurs a free induction decay (FID) of the magnetization associated with the excited nuclei.

Traditional Fourier Transform analysis transforms a time domain spectrum (amplitude of magnetization vectors vs. time) into a frequency domain spectrum (frequency vs. relative amplitude), which separates individual frequencies out of a multiphase spectrum. This separation can be used to advantage in studying the nuclei of interest. The duration of the pulses, the time between the pulses, the pulse phase angle and the composition of the sample are parameters, which affect the sensitivity of this technique.

International Patent Application No. WO9967606, incorporated herein by reference as if fully written out below, describes a check weighing system for samples on a production line, including a magnet for creating a static magnetic field over an interrogation zone to create a net magnetization within a sample located within the interrogation zone, and an RF coil for applying an alternating magnetic field over the interrogation zone to cause excitation of the sample according to the principles of NMR.

The use of NMR for techniques for check weighing samples on a production line encounters a variety of difficulties, including but not limited to the presence of interfering species such as metal particles either within the sample container or elsewhere in the system, effects of temperature on the magnet or electronics, humidity in the sample or system, and mechanical instability of the containers.

It would be desirable to provide a system and method for identifying and/or compensating for the above noted potential sources of imprecise measurements for an NMR sample check weighing system.

SUMMARY

The method relates to check weighing material contained in a container, which is passing along a product filling or production line, by nuclear magnetic resonance (NMR) techniques.

Many pharmaceuticals are packed in the form of blister packages. Optical techniques are used to determine presence, shape or color of the pills being packaged. With NMR techniques it is possible to determine the weight and even quality of the contents of this package.

The method provides means and methods for providing smooth transport of mechanically unstable containers through the NMR interrogation zone.

An improvement is provided in a magnetic resonance method for determining at least one property of multiple samples in a filling or production line, comprising:

applying a first magnetic field in a first direction in an interrogation zone for creating a net magnetisation within a sample located within the interrogation zone;

applying an alternating magnetic field in a second direction in the interrogation zone for temporarily changing the net magnetisation of the sample located within the interrogation zone; and monitoring energy emitted by the sample as the net magnetisation of the sample returns to its original state and generating an output signal having a characteristic which is proportional to the energy emitted;

characterised by:

introducing multiple samples into the interrogation zone simultaneously;

applying a gradient magnetic field to the interrogation zone wherein different positions within the interrogation zone are sensitive to different specific frequencies;

monitoring energy emitted by the samples in the different positions and generating an output signal having a characteristic which is proportional to the energy emitted corresponding thereto in different frequency bands; and, attributing the signals to specific positions and samples, and comparing the output signal characteristics of the specific positions and samples with like data obtained from at least one similar sample to provide an indication of the corresponding property of the samples.

An improvement is further provided in a magnetic resonance method for determining at least one property of a sample in a filling or production line, wherein the sample is contained in a mechanically unstable container, comprising:

applying a magnetic field in a first direction in an interrogation zone for creating a net magnetisation within a sample located within the interrogation zone;

applying an alternating magnetic field in a second direction in the interrogation zone for temporarily changing the net magnetisation of the sample located within the interrogation zone; and monitoring energy emitted by the sample as the net magnetisation of the sample returns to its original state and generating an output signal having a characteristic which is proportional to the energy emitted;

characterised by:

inducing mechanical stability to the container for movement through the interrogation zone.

Stability can be induced by providing pockets to hold the containers, optionally including placing and removing means; guiding the containers in a scrolling helical transport structure; carrying the containers in an array, optionally in a cassette system; adapting a conveyor belt to hold the containers while being transported through the interrogation zone; or feeding the containers through the interrogation zone without any inter-distance.

BRIEF DESCRIPTION OF THE DRAWINGS

FIG. 1a diagrammatically illustrates the form of a check weighing station according to an alternative embodiment in which a magnetic field gradient is applied over an interrogation zone.

FIG. 3A is a cross-sectional bottom plan view of the NMR probe containing compartment (or enclosure) with the conveyor belt return outside the probe.

FIG. 3B is a cross sectional side elevation view of the NMR probe containing compartment with the conveyor belt extending through the interrogation zone.

FIG. 3C is a plan view of the conveyor belt with in-feed and intermediate wheels to place vials of sample onto and remove vials of sample from the belt.

FIG. 4A is a cross-sectional bottom plan view of the NMR probe containing compartment with the conveyor belt return outside the probe.

FIG. 4B is a cross sectional side elevation view of the NMR probe containing compartment with the conveyor belt extending through the interrogation zone with wheels for counter-flexing the conveyor belt to eliminate belt speed fluctuations.

FIG. 6 is a schematic view of a conveyor belt engaging an in-feed wheel using spacers for exact vial positioning.

FIG. 7A is a schematic view of a conveyor belt engaging an in-feed wheel.

FIG. 7B is a side elevation view of a conveyor belt holding a ampule between polymeric spacers held by polymeric pins, engaging a drive or return wheel with timing holes for the pins of the belt.

FIG. 7C is a transverse cross sectional view of the conveyer belt and its under belt guide showing an ampule held in the belt.

FIG. 10A is a cross-sectional bottom plan view of the NMR probe containing compartment with the conveyor belt return outside the probe.

FIG. 10B is a cross sectional side elevation view of the NMR probe containing compartment with the conveyor belt extending through the interrogation zone carrying containers or packages (such as cassettes) of multiple syringes.

FIG. 10C is a schematic view of a sideward in-feed and out-feed of cassettes of multiple syringes onto the belt.

DETAILED DESCRIPTION

Figure 1:
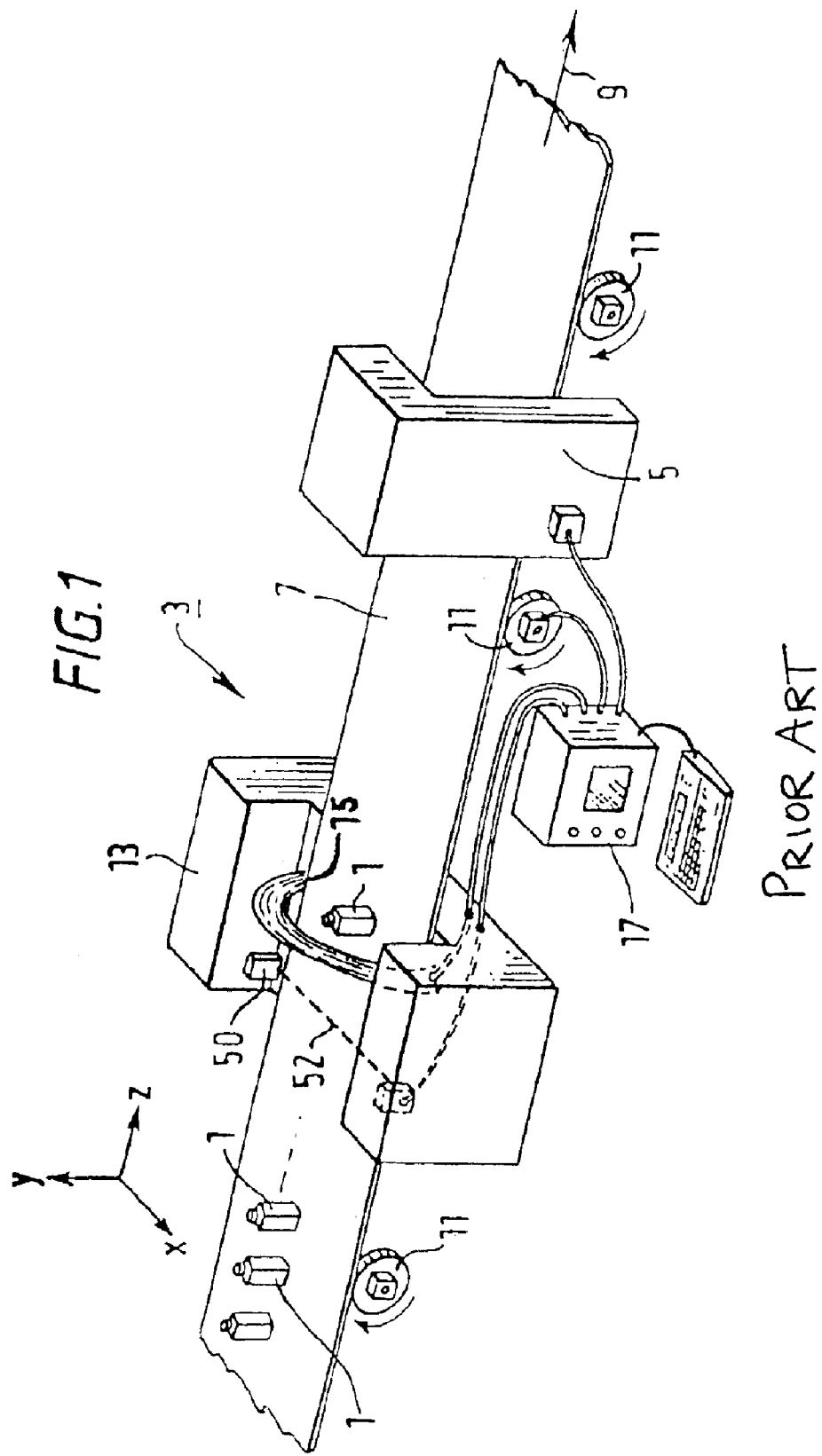
FIG. 1 is a schematic view of a production line with an NMR check weighing station for checking that each container passing through the weighing station has the desired amount of product.

The present methods relate to check weighing material contained in a container, which is passing along a production line, by nuclear magnetic resonance (NMR) techniques. As one example, check weighing is used by the pharmaceuticals industry for the monitoring and regulation of the amount of a drug in a sealed glass vial during filling. The drug weight can be as small as a fraction of a gram, and is required to be weighed with an accuracy of a few percent or better, in a vial weighing tens of grams at a rate of several weighings per second. Conventionally, to obtain the required accuracy, it is necessary to remove the vials from the production line and to weigh them on precision balances both before and after filling in order to take into account the weight of the container. Because this is time-intensive, only a fraction of the product can be tested. If deviations from expected values are detected, a large batch of product can be wasted before the problem is identified. As the vial must be weighed both before and after filling, the weighing must be performed in an aseptic environment between filling and sealing.

An NMR apparatus for determining the mass of a sample generally may comprise means for generating a static magnetic field in a first direction in the sample; means for applying an alternating excitation magnetic field in a second different direction in the sample; means for sensing energy emitted by the sample in response to the excitation magnetic field and for outputting a signal in dependence thereon; and means for comparing the signal output by said sensing means with stored calibration data to provide an indication of the mass of the sample. Such an apparatus can be used on-line in a product filling line. It can provide a non-contacting measure of the mass of the contents of a container independently of the container mass, if the container is made of a material which is not responsive to NMR, and is useful for determining the mass of small quantities of sample such as samples weighing between 0.1 grams and 10 grams which may be contained in glass containers of 20 grams or more, providing an indication of mass and not weight of the sample.

The apparatus can be used to measure the contents of a container by filling the container with the predetermined amount of sample; transporting each of the filled containers to a weighing station; weighing the sample within each of the containers; sealing the sample within the container; and rejecting any containers which do not contain the predetermined amount of sample within a predetermined tolerance.

The weighing of the sample includes generating a static magnetic field in a first direction in an interrogation zone for creating a net magnetization within a sample located within the interrogation zone; applying a pulse of alternating magnetic field in a second different direction in the interrogation zone for temporarily changing the net magnetization of the sample located within the interrogation zone; sensing energy emitted by the sample as the net magnetization of the sample returns to its original state and outputting a signal in dependence thereon; and comparing the signal output by the sensing step with calibration data which relates the mass of at least one similar sample of known mass to the corresponding signal output by the sensing step, to provide the indication of the mass of the sample within each container.

In addition to pharmaceuticals, such an apparatus and method can be used in a variety of applications, including but not limited to cosmetics, perfumes, industrial chemicals, biological samples and food products. It can measure high value products where 100% sampling can reduce wastage, and can be used to determine the mass of samples that are in solid form, in powder form, in liquid form and in gas form, or any combination thereof.

FIG. 1 shows a portion of a production line, which fills glass vials 1 with a drug sample. Included is a weighing station 3 that is provided "in-line" for weighing each of the filled vials that pass therethrough, and a reject station 5 that removes those vials from the line that do not have the sufficient amount of the drug to meet product specifications. The vials 1 are transported to the weighing station 3 from a filling (and optionally sealing) station (not shown) by a conveyor belt 7 which, as represented by the arrow 9, moves in the z direction through the action of rotating conveyor wheels 11. The weighing station uses NMR techniques to determine the mass of the drug sample within each of the glass vials 1. As those skilled in the art will appreciate, glass vials are useful as the container, because they do not give a signal that might interfere with the measurement process. In this embodiment, the weighing station 3 comprises a permanent magnet 13, an RF coil 15 and a computer control system 17. The magnet 13 is creates a homogeneous direct current (DC) or static magnetic field in the x direction across the conveyor belt 7. The sample in the glass vial contains nuclei which each possess a magnetic moment, e.g. 1H nuclei (protons). This magnetic moment, discussed above, is a result of the spin of the nuclei.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetization to rotate about the AC magnetic field's axis, away from the direction of the static field. In this embodiment, this magnetic field is generated by applying a corresponding AC current to the RF coil 15. The angle of rotation of the net magnetization can be varied by varying the amount of energy delivered to the RF coil 15.

In this exemplified embodiment, an excitation field that causes a 90° rotation is used to excite the sample. After the 90° pulse has been applied to the sample, the sample is left in a high-energy, non-equilibrium state, from which it will relax back to its equilibrium state. As it relaxes, electromagnetic energy at the Larmor frequency is emitted, the magnetic component of which induces current in the RF coil 15, the peak amplitude of which varies with, among other things, the number of magnetic moments in the sample and hence the number of molecules in the sample. The received signal is then passed to the computer control system 17, which compares the peak amplitude of the signal received from the unknown sample, with the peak amplitude of a signal received from a calibration sample with a known mass (or weight), to determine the mass (or weight) of the sample being tested. The check weighing station 3 may be able to generate and receive signals at different Larmor frequencies needed to be able to excite different NMR responsive elements in samples. If the computer control system 17 can store calibration data for each of the different samples, then the check weighing station would be able to determine the mass of various samples using the NMR signals from the different NMR responsive elements.

The operation of one embodiment is described in detail with reference to FIG. 1f, a block diagram of the principal components of the computer control system 17 of this embodiment. The control system comprises a connection terminal 21 for connecting the control system to the RF coil 15. The connection terminal 21 is connectable, through switch 23, to a signal generator 25 and a power amplifier 27 which are operable to generate and amplify respectively the excitation signal which is applied to the RF coil 15. The connection terminal 21 is also connectable, through the switch 23, to a receiving amplifier 31 which amplifies the signal received from the sample under test. This amplified signal is then filtered by the filter 33 to remove noise components and then passed to the mixer 35 where the received signal is down converted to an intermediate frequency (IF) by multiplying it with an appropriate mixing signal generated by the signal generator 25. The IF signal output by the mixer 35 is then filtered by the filter 37 to remove the unwanted components generated by the mixer 35. The filtered IF signal is then converted into a corresponding digital signal by the A/D converter 39 and is then passed to the microprocessor 41.

As shown by the dashed control lines 43 and 45, the microprocessor 41 controls the operation of the signal generator 25 and the switch 23. The microprocessor 41 may operate to ensure that the signal generator 25 generates the excitation signal when the filled vial 1 is at the desired location within the check weighing station 3. The microprocessor 41 knows when the vial 1 is at the correct location from a signal received from the position sensor electronics 47 which is connected, through connection terminal 49, to an optical position sensor 50 mounted in the check weighing station 3. Referring to FIG. 1, when the glass vial 1 passes by the optical position sensor 50, a light beam 52 is broken. This is detected by the position sensor electronics 47 which in turn signals the microprocessor 41. Based on this information and the speed of the conveyor belt 7 (provided by the conveyor controller 51), the microprocessor determines the appropriate timing for the application of the burst of excitation current and signals the signal generator 25 accordingly.

As those skilled in the art of magnetic resonance will appreciate, it takes a finite period of time after the sample enters the static field generated by the magnet 13 for the net magnetisation of the sample to develop along the X-direction. If the excitation signal is applied to the RF coil 15 before the magnetisation has fully developed, then the strength of the signal generated by the sample will not be at its maximum.

The net magnetisation and thus the strength of the resultant signal produced by a sample varies with time in the static magnetic field. The longitudinal relaxation time depends upon the sample being tested and the strength of the static magnetic field. Therefore, given the strength of the static magnetic field and the type of sample which is being tested, the relaxation time can be determined. This information, combined with the speed of the conveyor belt 7, determines the minimum length of the magnet 13 in the Z-direction which is required to ensure that as large a signal as possible is generated by the sample under test.

In one embodiment, a capacitor (not shown) is connected across the ends of the RF coil 15 so that it is tuned to the Larmor frequency of the sample. The Larmor frequency of an MR responsive element such as hydrogen is calculated by multiplying the static magnet's DC magnetic field strength by the gyromagnetic ratio for the element (which for hydrogen is 42.57 MHz/Tesla). The gyromagnetic ratio for other MR responsive elements can be found in CRC Handbook of Chemistry & Physics, published by CRC Press Inc. The Larmor frequency of an MR responsive element such as hydrogen is calculated by multiplying the static magnet's DC magnetic field strength by the gyromagnetic ratio for the element (which for hydrogen is 42.57 MHz/Tesla). The gyromagnetic ratio for other MR responsive elements can be found in CRC Handbook of Chemistry & Physics, published by CRC Press Inc. The tuning of the RF coil 15 in this way makes the system less susceptible to electromagnetic interference or to other MR signals from nuclei with different gyromagnetic ratios. The excitation current flowing through the RF coil 15 generates a corresponding magnetic field in the Z-direction. This excitation magnetic field causes the net magnetisation of the sample in the vial 1 to rotate or precess about the X-axis at the Larmor frequency. When the excitation current is removed from the RF coil 15, the nuclei in the sample begin to relax back to their equilibrium positions, emitting RF energy at the Larmor frequency as they do so. This induces a signal in the RF coil 15 which is seen to decay and its characteristic time is referred to as the transverse relaxation time. This depends upon the sample being tested and not on the static field strength.

As shown, the peak amplitude of the induced signal is at its maximum shortly after the excitation current stops, after which point the signal decays to zero. The peak amplitude of the signal induced in the RF coil 15 by the sample is directly proportional to the number of magnetic moments in the sample. Consequently, in this embodiment, the microprocessor 41 monitors the peak signal level which it receives from the A/D converter 39 after the excitation signal has been removed from the RF coil 15. Alternatively the microprocessor can determine the average signal over a period of time or fit the shape of the curve in order to improve accuracy.

In one embodiment, the microprocessor 41 then compares this peak signal level with calibration data obtained by testing a similar sample or samples of known mass, to provide an indication of the mass of the sample currently being tested. In this embodiment, this calibration data is obtained from a number of similar samples of different known masses during a calibration routine before the production batch is begun and is stored in memory 53. In this embodiment, the calibration data is a function which relates the peak amplitude of the MR signal received from the sample under test to the mass of the sample.

As described in the embodiments above, the RF probe monitors the energy emitted by the sample as the net magnetisation of the sample returns to its original state of equilibrium, and generates an output signal having a characteristic that is proportional to the energy emitted, such as current amplitude. The computer control system receives the RF probe output signal. A processor compares the current amplitude or other output signal characteristic with like data obtained from at least one similar sample of known mass, and determines the mass of the sample from the results of the comparison. It is to be understood that although for purposes of illustration the embodiment has been described as measuring the peak amplitude of the induced signal, any chemometric characterization technique can be used that derives a single value from the energy emitted and the output signal generated. In general, comparison techniques may include comparing the FID characteristics of the sample with like FID characteristics of at least one known sample, i.e., the calibration data.

In one embodiment, if the microprocessor 41 determines that the mass of the current sample being analysed is not of the required mass within a given tolerance, it outputs a control signal on control line 55 to the reject controller 57. The reject controller then outputs a signal to output terminal 59 which is connected to the reject station 5, for causing the reject station to remove the current vial 1 being tested from the conveyor belt 7 when it arrives at the reject station 5.

Figure 1B:
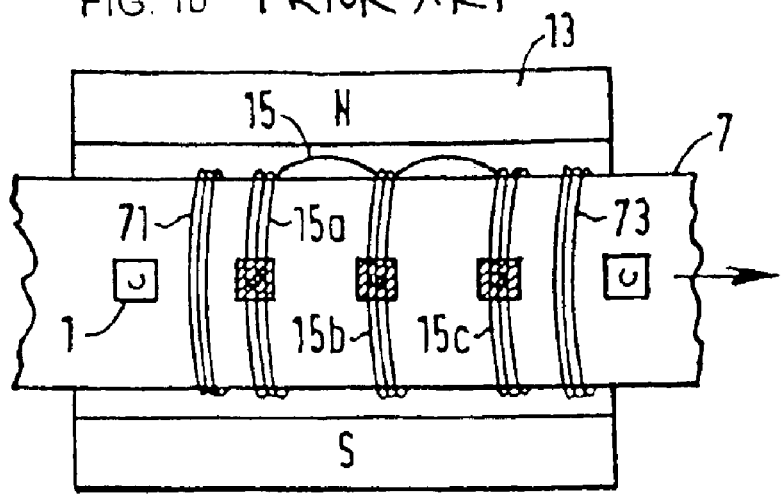
FIG. 1b diagrammatically illustrates an alternative check weighing station.
Figure 1C:
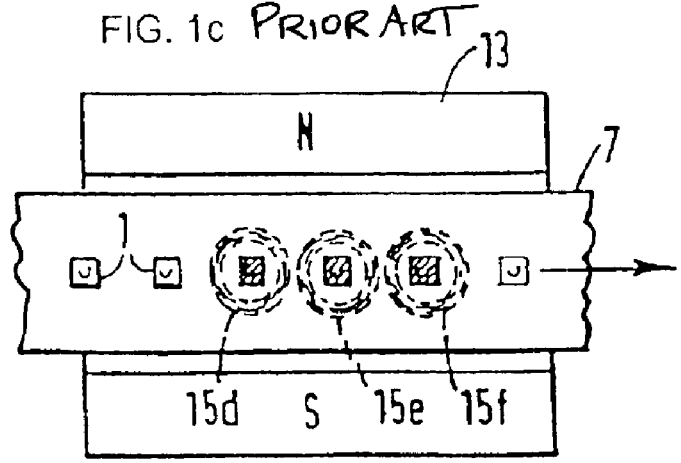
FIG. 1c illustrates a further check weighing station.
Figure 1D:
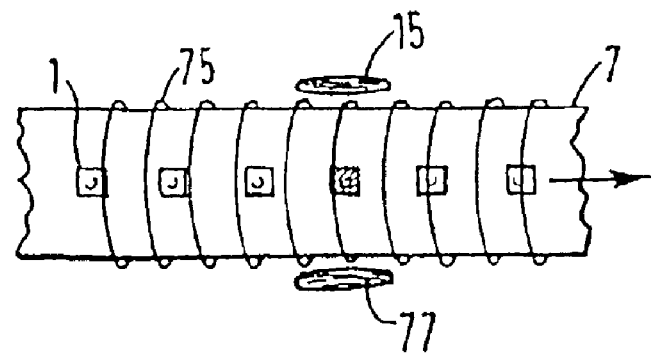
FIG. 1d illustrates another check weighing station.
Figure 1E:
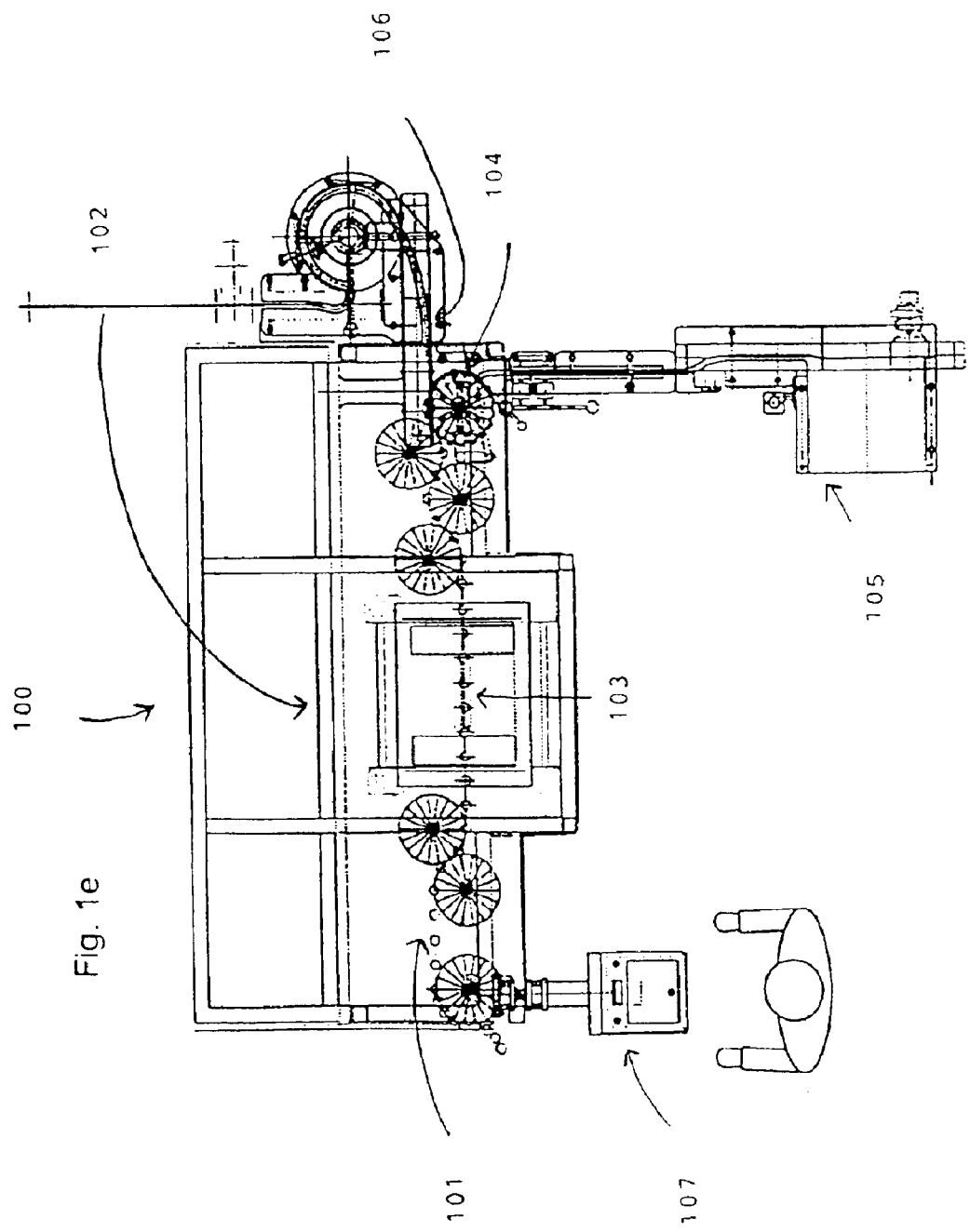
FIG. 1e is a schematic plan view of a production line with an NMR check weighing station
Figure 1F:
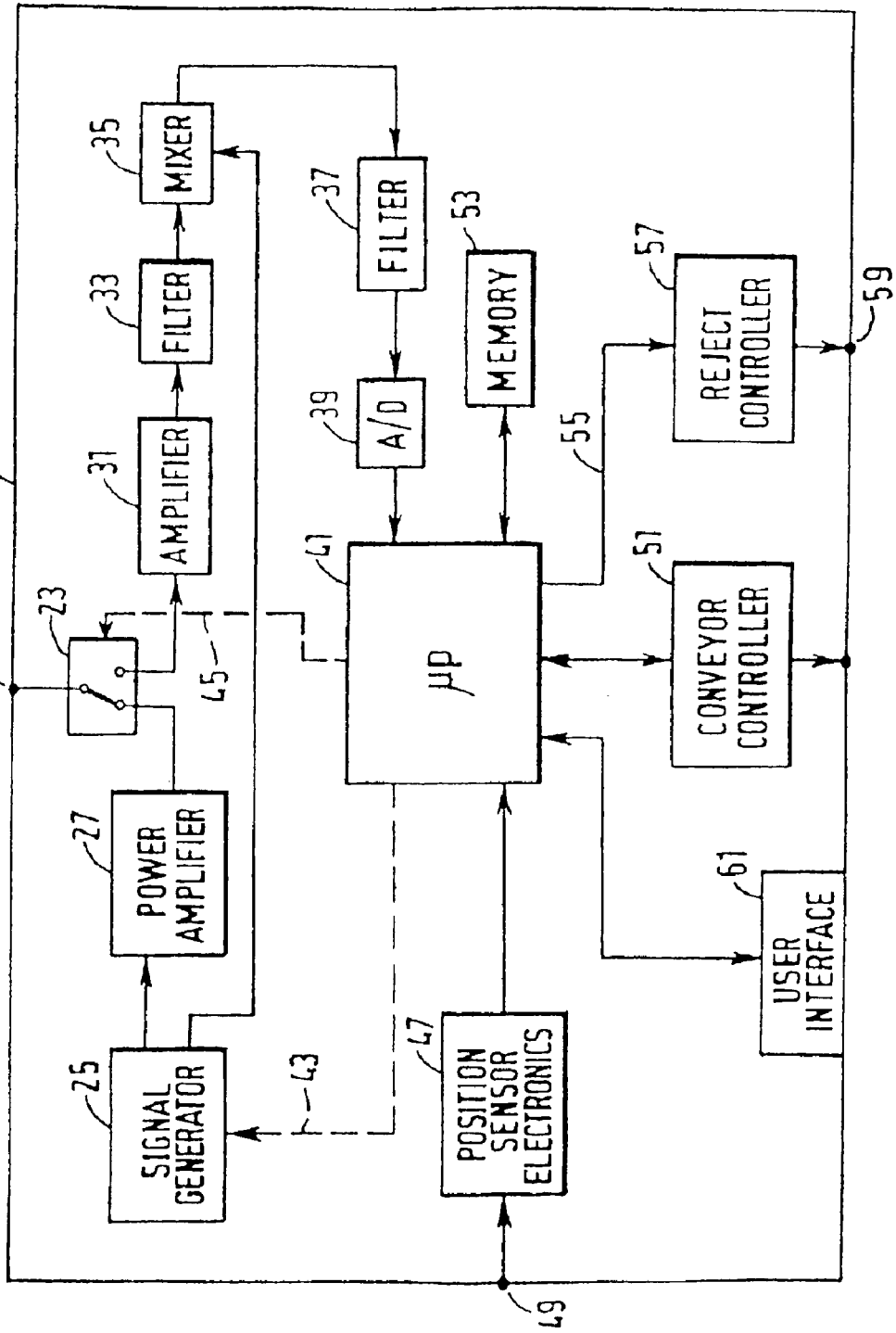
FIG. 1f is a block diagram of excitation and processing electronics that form part of and control the check weighing station shown in FIG. 1.

As shown in FIG. 1f, the computer control system 17 may also comprise a user interface 61 for allowing the user to program into the control system 17 what the correct mass of each sample should be for a given batch of product.

In certain embodiments, a single measurement of a sample's mass is determined for each vial. The accuracy of the measurement can be improved by taking an average of repeated measurements. However, the rate at which measurements can be made on the same sample is determined by the relaxation time discussed above. In particular, after the excitation signal has been removed, it takes approximately 3 times the relaxation time for the protons to return to their original aligned state in the static magnetic field, at which point a further burst of excitation current can be applied.

Separate measurements could be obtained either by using a number of different RF coils spatially separated along the Z-direction. Alternatively, the conveyor belt could be stopped each time a vial reaches the interrogation area and multiple measurements made.

Multiple measurements of the same sample may also be possible if the interrogation zone of the magnet and RF coil is large enough to allow multiple measurements to be taken considering the speed of the conveyor belt. In such an embodiment, the accuracy of the system will depend upon the homogeneity of the RF coil and the magnetic field within the interrogation zone as well as on the system signal to noise and the RF coil's fill factor. If the field patterns of the magnet and RF coil are known in advance, then this knowledge can be used to make corrections on the different measurement signals. Also, additional X, Y and Z coils (known in the art as shims) may also be provided to improve the homogeneity of the static magnetic field.

In one embodiment, a single vial is located within the RF coil 15 interrogation zone at any one time. FIG. 1a diagrammatically illustrates another embodiment in which the components of a check weighing station 3 allow multiple vials to be located within the RF coil 15 interrogation zone at the same time and which allow a mass measurement to be made of the sample within each vial individually. To achieve this, in such embodiment, in addition to the static magnet 13 and the RF coil 15, a separate pair of coils 71 and 73 are located either side of the conveyor belt 7, which operate to provide a magnetic field gradient across the conveyor belt 7. As a result of this gradient, the static magnetic field experienced by each of the glass vials will be different and thus the Larmor frequency of the sample in each of the three vials in the interrogation zone will be different. Consequently, each vial can be interrogated separately by applying three different narrow band RF pulses at the appropriate Larmor frequency.

Alternatively, a broad band RF pulse could be applied over the interrogation zone and the resulting MR signals from the samples can be resolved by taking the Fourier transform of the received signal after the excitation pulse has ended, as is standard practice in MR imaging.

With reference to FIG. 1a, the gradient coils are arranged to apply a gradient in the same direction as the static magnetic field which is generated by the magnet 13. As is well known in the art of magnetic resonance imaging, gradient coils can be arranged to provide magnetic field gradients in one or more of the X, Y or Z axes so that the entire volume of the interrogation zone can be spatially resolved. FIG. 1b illustrates an embodiment where the two gradient coils 71 and 73 are provided at opposite ends of the RF coil's interrogation zone. In this embodiment, the RF coil 15 comprises three separate portions 15a, 15b and 15c. As those skilled in the art will appreciate, by applying a magnetic field gradient along the length of the conveyor belt 7 through the interrogation zone, each of the samples can be interrogated separately or simultaneously in the same way as in the embodiment described with reference to FIG. 1a.

In the embodiments described with reference to FIGS. 1a and 1b, a plurality of samples were located within the interrogation zone and either interrogated separately or simultaneously. In these embodiments, since each of these samples will experience a slightly different magnetic field and will be in a different position relative to the RF coil, separate calibration data can be used for each of the sensing positions in order to try to reduce errors caused by inhomogeneities in the static magnetic field or in the RF coil.

In the above embodiments, the RF coil generated a magnetic field in the Z-direction along the direction of movement of the conveyor belt 7. The RF coil can be located at any angle relative to the DC magnetic field, provided the field which it generates is relatively homogenous over the sample being tested and provided it comprises a component which is orthogonal to the static magnetic field. FIG. 1c diagrammatically illustrates an embodiment where three separate RF coils 15d, 15e and 15f are provided under the conveyor belt 7, each of which is operable to generate an AC magnetic field in the Y-direction. This embodiment allows the samples in three vials to be tested simultaneously. It also allows the system to interrogate the sample in each vial three times, once by each of the RF coils.

In the above embodiments, a permanent magnet was used to generate the static magnetic field. As those skilled in the art will appreciate, electromagnets, current carrying coils or superconducting magnets could be used in place of the permanent magnet to generate the necessary DC magnetic field. Additionally, in the above embodiments, the DC magnetic field was applied across the conveyor belt in the X-direction. As those skilled in the art will appreciate, the DC magnetic field can be applied through the sample in any direction. For example, the north and south pole of the magnet may be placed above and below the conveyor with the RF coil being, for example, in the same orientation as in the first embodiment. FIG. 1d shows yet another embodiment in which a solenoid coil 75 is wound along a length of the conveyor belt 7 for generating the static magnetic field along the length of the conveyor belt 7, i.e. in the Z-direction. In this embodiment, the RF coil 15 is provided at one side of the conveyor 7 and a separate detector coil 77 is provided at the opposite side of the conveyor 7.

Continuous, non-contact weighing of products materials in vials.

FIG. 1e shows a schematic plan view of a production line employing an NMR check weighing station for weighing vials, or other similar containers, in which multiple samples of product materials enter the interrogation zone simultaneously. Generally, the check weighing station 100 includes an in-feed section 101 comprising a conveyor or other transport mechanism, a check weighing section 102 containing the magnet, RF antenna (or NMR probe), and in part, defining the interrogation zone 103, a reject section 104 leading to a reject buffer 105, and an out-feed section 106. The check weighing station 100 may contain an operator panel 107.

Figure 2:
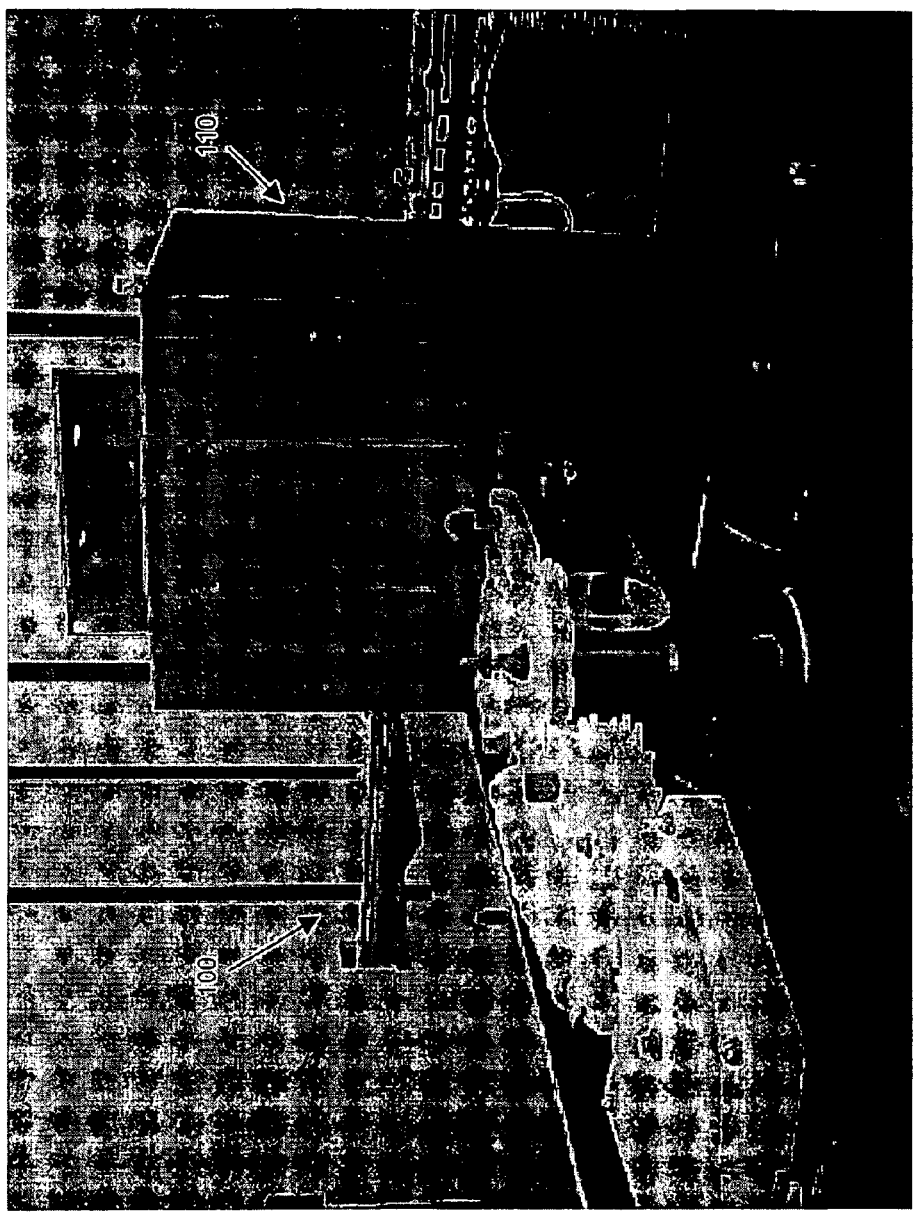
FIG. 2 is a photograph of a conveyer line leading to an NMR probe within an enclosure having an access port to the interrogation zone for containers of samples for measurement.

In FIGS. 2–6, the components of the check weighing station 100 are shown in more detail. For example, FIG. 2 is photograph of a conveyor line (which is part of the in-feed section 101) leading to the check weighing section 102, wherein the check weighing section 102 is defined by an enclosure 110 (FIGS. 3A–3C, 4A and 4B). As seen in FIGS. 3A and 4A, the permanent magnet is contained within the check weighing housing 111, the NMR probe is generally indicated by the numeral 112, and both are provided within the enclosure 110.

The bore size of the magnet allows a transportation means for the products that are to be measured. Inside the magnet, the NMR probe 112 acts as a radio-frequency electromagnetic emitter/receiver that both excites the material and receives the response. The construction of the NMR probe 112 is such that there is maximum allowance for transportation mechanisms to carry products through the system.

To determine the weight of a specific product, a characteristic, such as the amplitude, of the response signal is used. To determine the specific responses related to more than one product in the measurement volume, it is possible to use special magnetic fields with gradients. These fields cause positions to be sensitive to, specific frequencies. With the use of gradient magnetic fields, product at different positions will generate NMR signals that can be separated in different frequency bands. The signal content per frequency band can then be attributed to the specific product/position. By using the shape of the response curve, several quality aspects of the contents can be monitored, like product degradation and composition of the active ingredient. For example, a standardized, known calibration sample is used to determine a 'template' FID in order to provide calibration data. Known NMR techniques used in chemical analysis to compare shapes of curves in a quantitative manner are used to provide the comparison.

To transport product materials contained in vials through the enclosure 110, a conveyor belt 113, as seen in FIGS. 3B and 4B, is provided through the enclosure 102, and is used to smoothly transport vials from the in-feed section 101 (located upstream of the enclosure 102 in FIG. 1E) to the reject section 104 (located downstream of the enclosure 102 in FIG. 1E). The conveyor belt 113 serves as a carrier for the vials, and is constructed from materials selected from a group including Kevlar®, Teflon®, polyester, polyurethane, aramide, glass, or other thermoplastic materials. To feed the vials through the NMR probe 112, the conveyor belt 113 travels through the NMR probe 112 from the in-feed section 101. As seen in FIGS. 3B and 4B, the conveyor belt 113, when returned along the second horizontal plane 114B, travels outside (and underneath) the NMR probe 112.

The in-feed section 101 includes an in-feed wheel 115 which is configured to receive various vials from the remainder of the in-feed section 101. As seen in FIGS. 3C and 6, the in-feed wheel 115 includes various receiving indentations 116 which are spaced around the circumference of the in-feed wheel 115, and are ideally sized to receive individual vials.

Rotation of the in-feed wheel 115 (counter-clockwise as seen in FIG. 3C) allows the individual vials to be transferred to the conveyor belt 113 in a spaced relationship. More specifically, as the in-feed wheel 115 rotates, the spacing of the receiving indentations 116 facilitates placement of the vials 116 in a spaced relationship along the conveyor belt 113.

Further facilitating spacing of the vials along the conveyor belt 113 are various spacer pairs 118. The spacer pairs 118 are provided in spaced intervals along the conveyor belt 113 to define receiving areas 120 therebetween. The spacer pairs 118 are attached to the conveyor belt 113 using pins 122. The spacer pairs 118 and pins 122 can be constructed of polyoxymethylene (POM) and/or polyvinylchloride (PVC).

Figure 5B:
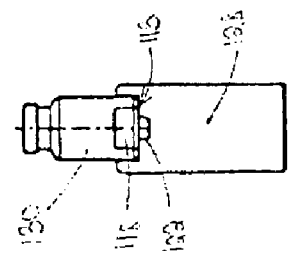
FIG. 5B is a transverse cross sectional view of the conveyer belt and its under guide showing a vial held in the belt.

In addition to attaching the spacer pairs 118, the pins 122 are also provided to interface with timing holes 123 provided on a first drive wheel 124 (provided downstream of the enclosure 102) and a second drive wheel 125 (provided downstream of the enclosure 102). The cooperation of the pins 122 with the timing holes 123 provided on the first drive wheel 124 and second drive wheel 125 provides for movement of the conveyor belt 113. As seen in FIG. 4B, a first supplementary wheel 126 and a second supplementary wheel 127 can be provided to counterflect the conveyor belt 113, and reduce speed fluctuations of the conveyor belt 113. Counterflection of the conveyor belt 113 thereby provides for additional consistency in the spaced relationship of the vials along the conveyor belt 113. Moreover, as seen in FIGS. 3B, 4B, 5A, and 5B, an under guide 128 is provided to maintain movement of the conveyor belt 113 and the vials supported thereon in the horizontal plane 114A. The under guide 128 is also used to maintain the transverse position of the conveyor belt 113 as seen in FIG. 5B.

Figure 5A:
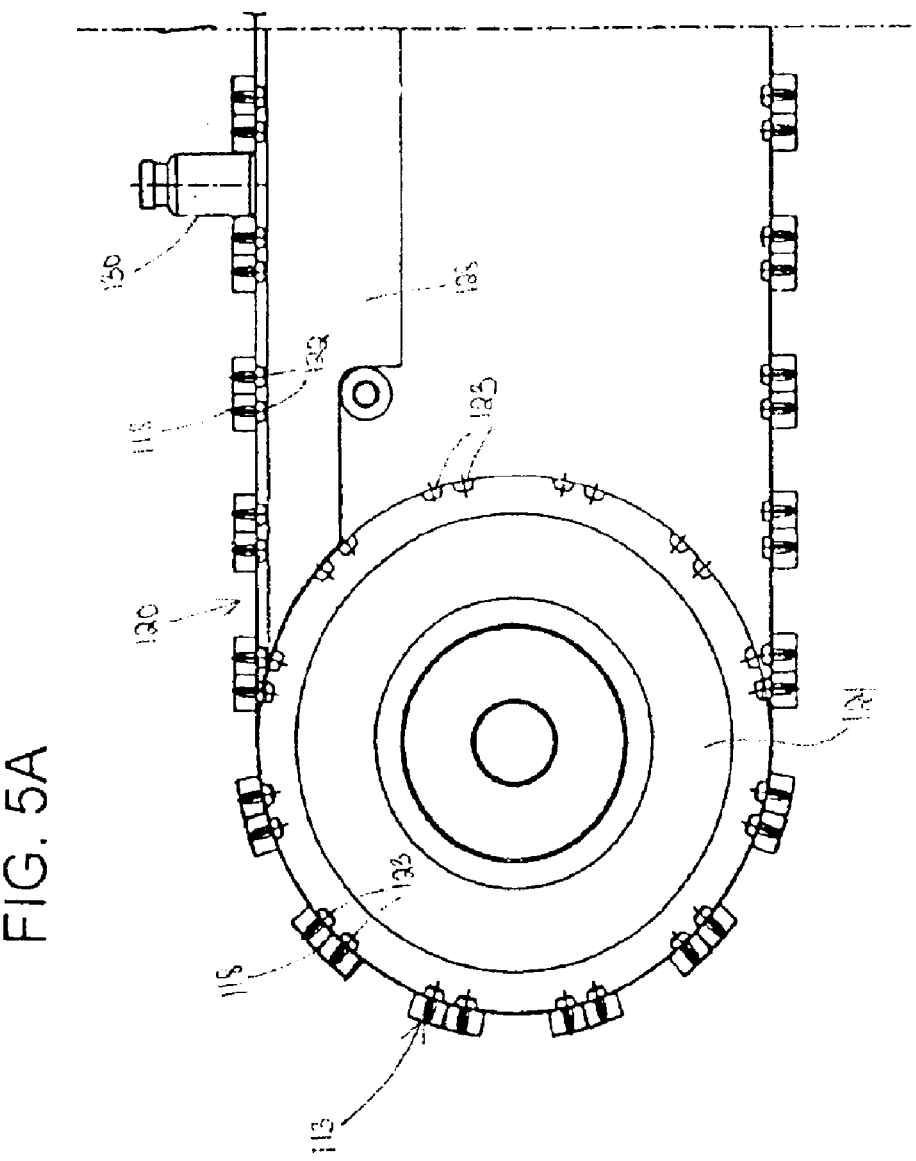
FIG. 5A is a side elevation view of a conveyor belt holding a vial between polymeric spacers held by polymeric pins, engaging a drive or return wheel with timing holes for the pins of the belt.

As seen in FIG. 5A, the spacing between the spacer pairs 118, and therefore, size of the receiving areas 120 is adapted to match the diameter of the vials (one of which is indicated by the numeral 130 in FIGS. 3B, 4B, 5A and 5B). Therefore, as the vials 130 are transferred from the in-feed wheel 115, the conveyor belt 113 is configured to receive individual vials 130 between the spacer pairs 118 and in receiving areas 120. When the vials 130 are located in the receiving areas 120, the vials 130 are properly spaced for travel along the conveyor belt 113 through the interrogation zone 103, and more specifically, through the NMR probe 112.

After analysis of the vials 130 in the interrogation zone 103, the vials 130 are removed from the conveyor belt 113 by an intermediate wheel 132. The intermediate wheel 132 can be part of the reject station 104. Like the in-feed wheel 115, intermediate wheel 132 (FIG. 3C) includes various receiving indentations 116 which are spaced around the circumference thereof, and are ideally sized to receive individual vials. Rotation of the intermediate wheel 132 (counter-clockwise as seen in FIG. 3) allows individual vials 130 from the conveyor belt 113 to be received in the receiving indentations 116 to thereafter be removed to the remainder of the reject station 104. The reject stationer 104, as seen in FIG. 1E, is configured to separate the vials 130. Those vials 130 that have been rejected by the interrogation process are directed to the reject buffer 105, and those vials 130 that have not been rejected are directed to the out-feed section 106.

However, there are other configurations of the NMR check weighing station which will allow a measurement of the mass of the sample (contained in containers other than vials 130, such as blister packs, ampules and syringes) to be obtained.

Continuous, Non-contact Weighing of Products Materials in Ampules, Syringes, and Blister Packages The application of NMR technology for determining weight or other properties of product materials (i.e. fluid pharmaceutical products) contained in vials is discussed above. As discussed above, it is preferred that vials are smoothly transported through a specific set-up designed for the NMR measurement. However, it is currently not possible to determine the other properties of product materials contained within ampules or syringes in a non-destructive way. Even using the NMR check weighing station set-up described above, it is not possible to determine characteristics of ampules or syringes due to the mechanical instability of these containers. As such, there does not currently exist a non-destructive method for determining the weight or other properties of the contents of ampules and syringes.

NMR has already been shown to be applicable as a technology to determine weight or other properties of product materials. However, as discussed above, ampules and syringes are both more difficult to handle than ordinary vials. Furthermore, in current production environments, they also are usually transported in arrays or a matrix. As an improvement on the method of using NMR for non-contact, non-destructive measurement of materials such as liquids and/or powders in glass vials as described above, the NMR check weighing station can be adapted to use NMR techniques for measurement of product materials in ampules and syringes. Two aspects are disclosed herein. The first focuses on specific solutions which are adapted to handle simultaneous movement of multiple ampules or syringes through the interrogation zone 103, and the second focuses on the measurement of product materials contained in multiple containers arranged a matrix (i.e. various rows of containers). Due to the second aspect, application of gradient fields can be used for already multiply packed containers (including vials, ampules and syringes), for example, for inspecting products in stock.

As discussed above, ampules and syringes are highly unstable mechanically. Therefore a specially-configured conveyer belt may be adapted to hold the containers while being transported through the system. For example, as seen in FIGS. 7A–7C, it is difficult to carry ampules (generally indicated by the numeral 140) using the conveyer belt 113 used for carrying vials 130. Although the receiving areas 120 can be matched to the dimensions of the ampules 140, the center of gravity of certain ampules 140 may be too high. Therefore, if the ampules 140 are placed in the receiving areas 120 between the spacers pairs 118, the ampules 140 may tip over as the conveyer belt 113 (and the multiple ampules 140 contained thereon) is moved through the enclosure 110 and interrogation zone 103.

Multiple ampules 140 (FIGS. 8A and 8B) and syringes (generally indicated by the numeral 142 in FIGS. 9A and 9B) may be simultaneously moved through the enclosure 110 and interrogation zone 103 by a specially-configured conveyer belt 143. The conveyer belt 143 serves as a carrier for the ampules 140 or syringes 142, may include "hour glass" shaped spacers 144 which hold the ampules 140 and syringes 142 in a manner to overcome their inherent mechanical instability. As discussed above, and as seen in FIGS. 8B and 9B, the under guide 128 is provided to insure that the conveyer belt 143 and the spacers 144 supporting the ampules 140 and/or syringes 142 are supported in the horizontal plane 114A.

Figures 8A, 8B:
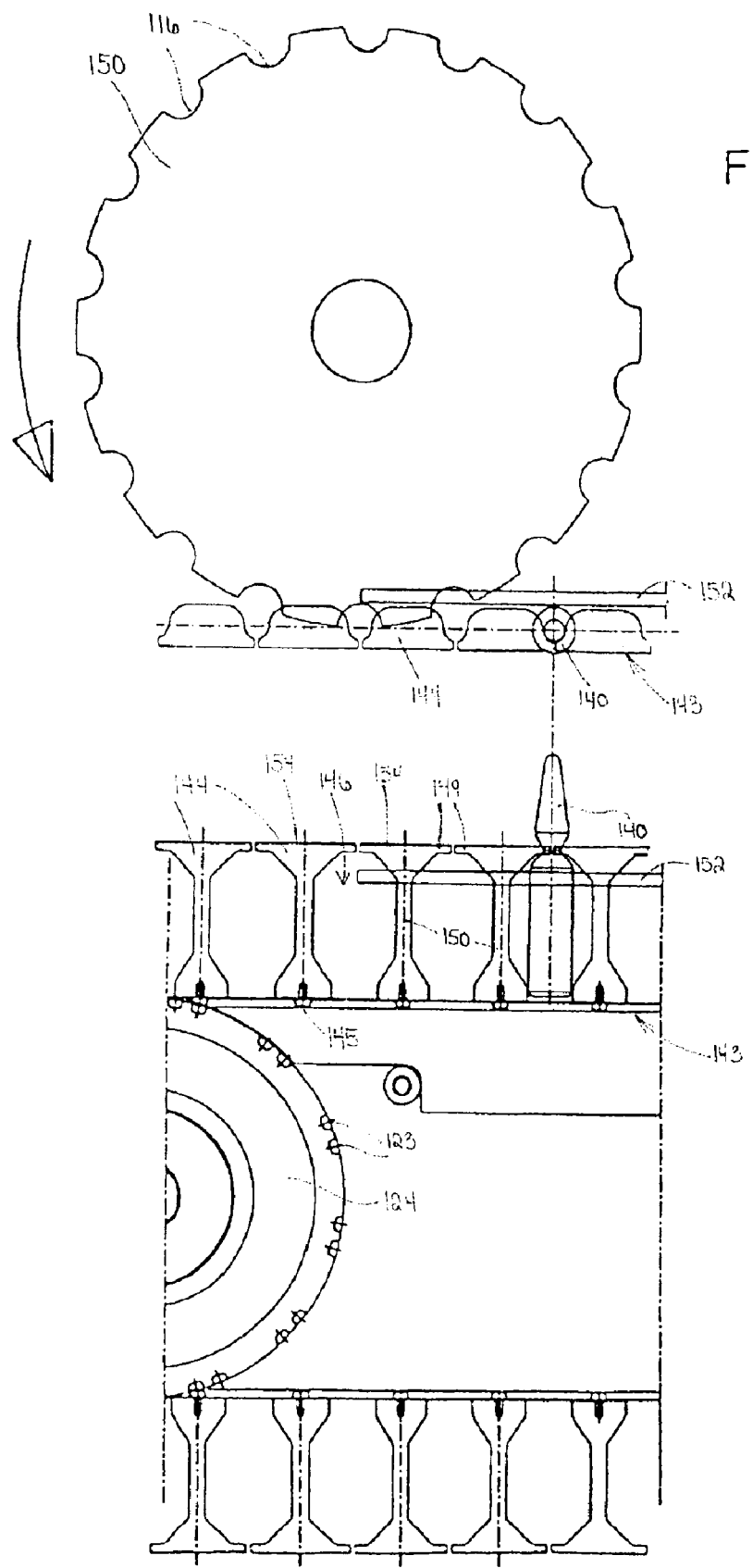
FIG. 8A is a schematic view of a conveyor belt, engaging an in-feed wheel, using spacers for exact ampule positioning between necks of adjacent spacers with a side guard to prevent the ampules from falling out of the carrier.
FIG. 8B is a side elevation view of a conveyor belt holding an ampule between polymeric spacers held by polymeric pins, engaging a drive or return wheel with timing holes for the pins of the belt and spacers for exact ampule positioning between necks of adjacent spacers with a side guard to prevent the ampules from falling out of the carrier.
Figure 9A:
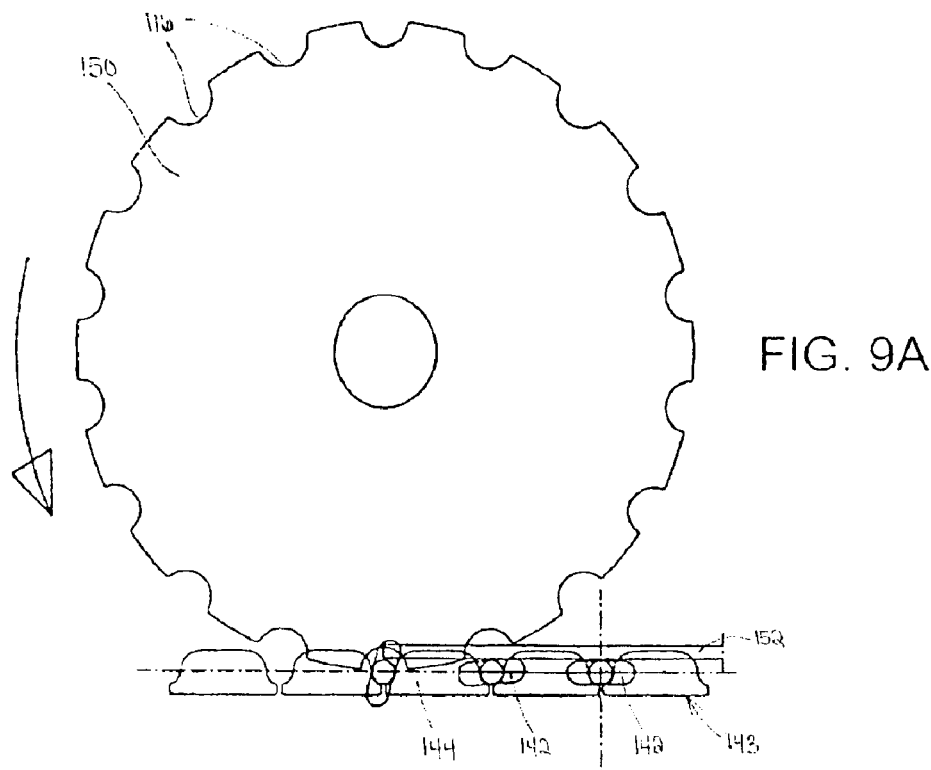
FIG. 9A is a schematic view of a conveyor belt, engaging an in-feed wheel, using pins spacers for exact syringe positioning between necks of adjacent spacers with a side guard to prevent the syringes from falling out of the carrier.
Figure 9B:
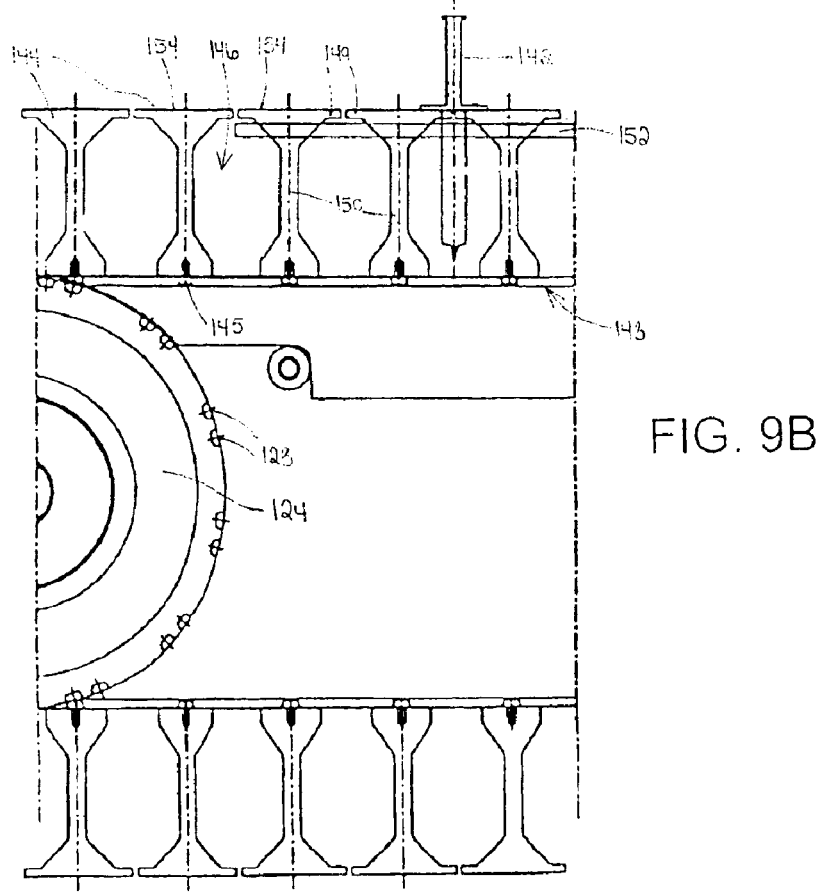
FIG. 9B is a side elevation view of a conveyor belt holding a syringe between polymeric spacers held by polymeric pins, engaging a drive or return wheel with timing holes for the pins of the belt and spacers for exact syringe positioning between necks of adjacent spacers with a side guard to prevent the syringes from falling out of the carrier.

As best seen in FIGS. 8B and 9B, the spacers 144 are spaced adjacent one another along the conveyer belt 113, and are fastened to the conveyer belt 113 using pins 145. The pins 145 can cooperate with the first drive wheel 124 and second drive wheel 125 in the manner described above to drive movement of the conveyer 143.

The spacers 144 are separated by gaps which define pockets (or receiving areas) 146 for receiving the ampules 140 and syringes 142. The pockets 146 are formed between webs 148 and between necks 149 of adjacent spacers 144, and allows the ampules 140 and syringes 142 to be placed between adjacent spacers 144 by an in-feed wheel 150 (FIGS. 8A and 9A) in a spaced relationship as discussed above.

As an alternative to the in-feed wheel 150, the ampules 140 and syringes 142 can be placed between the spacers 144 by a vacuum suction cups that catch the ampules and syringes on top, or by mechanical lifting mechanisms (either can be embodied in a pick and place robot). Moreover, a long scrolling helical structure can be provided to guides the ampules and syringes along the production line instead of the conveyer belt 143. The long scrolling helical structure can guide the ampules 140 or syringes 142 through the enclosure 110 and into the interrogation zone 103.

During movement along the conveyer belt 143, the ampules 140 and syringes 142 are stabilized because the portion of the pockets 146 between the necks 149 is relatively small, and the ampules 140 and syringes 142 are effectively clamped therein. Moreover, as seen in FIGS. 8B and 9B, side guides 152 are used to maintain the ampules 140 and syringes 142 in position in pockets 136 along the conveyer belt 143 after placement by the in-feed wheel 150, and the ampules 140 and syringes 142 are carried by the upper surfaces 154 of the spacers 144 to allow a significant portion of the ampules 140 and syringes 142 to float in the portion of the pockets 146 between the webs 148. As such, the inherent instability of the ampules 140 and syringes 142 is overcome (and mechanical stability is induced) using the conveyer belt 142 with the spacers 144 defining the pockets 146. Therefore, materials contained in individual rows of vials (as discussed), ampules 140 and syringes 142 can be moved through the enclosure 110 and the weight or other properties of these materials can be measured in the interrogation zone 103.

As an alternate to the conveyer belt 143 and the spacers 144 provided therealong, cassettes (as seen in FIGS. 10A–10C) generally indicated by the numeral 160 can be used. The cassettes 160 are carriers configured to house multiple ampules 140 or syringes 142 in a spaced relationship, and to simultaneously move these ampules 140 or syringes 142 through the enclosure 110 and into the interrogation zone 103. As seen in FIG. 10C, the cassettes 160 can be transported to and away from a conveyer belt 163 by an in-feed conveyer 164 (as part of the in-feed section 101) and an out-feed conveyer 165 (as part of the reject section 105). Moreover, the conveyer belt 163 does not require spacers of the sort described above, but is configured to transport the cassettes 160 through the enclosure 110 and into the interrogation zone 103 in the manner described above.

Alternatively, blister packages, blow-fill-seal packages, and bags can be used provided that a conveyer belt is adapted accordingly, or individual containers (including vials 130, ampules 140 and syringes 142) can be fed through the system without any inter-distance between neighboring containers. For example, multiple blister packages can be attached to one another (to form one blister pack serving as a carrier), and these blister packages can simultaneously be feed through the enclosure 110 and into the interrogation zone 103 along a conveyer belt. As the spacing between the product materials is pre-determined given the configuration of the blister packages, the above-described specially configured conveyer belt 113 or conveyer belt 143 are not necessary. The second alternative (in place of the conveyer belt 113 for vials 130 and conveyer belt 142 for ampules 140 and syringes 142) resembles a bottling line where multiple containers are fed through the enclosure 110 and into the interrogation zone 103 simultaneously, and the containers themselves are used to keep each other in the right position. The second alternative requires specific arrangements of the NMR system. The NMR system must be configured to filter out cross-coupling effects from neighboring containers, and can either be done by designing the transmitter/receiver (NMR probe) such that only one sample is being excited and measured at a time, or by applying gradient magnetic fields to separate containers by frequency band.

When measuring the weight or other properties of materials contained within the syringes 142, a specific problem is posed when metal needles are fitted to the syringes. Usually metals, either ferrous or non-ferrous, do influence the field and the frequency that is created by the transmitter. Therefore, special arrangements should be made to the transmitter and corresponding electronics so that they can be adapted to be insensitive to metals, and have limited effects on the magnetic resonance measuring methods.

As such, the magnetic resonance measuring methods can also be adapted for presence of other container components, such as metal caps. Without special arrangements, the presence of metal caps will, as discussed above, affect the functionality of the NMR probe. Two of the possible ways to accommodate this include but are not limited to the following. First, where the resulting effect on the NMR signal from the product is negligibly small (related to the Signal/Noise ratio) or the effect is invariant from cap-to-cap, it is possible to calibrate the measuring system with the inclusion of capped products. Second, it is possible to design the conductor pattern in the probe such that the emission region is limited in height so as not to excite the cap material.

In addition, the magnetic resonance measuring methods can be adapted for presence of container closure means, such as rubber stoppers. Like other solid components, the T2 (spin-spin relaxation) of rubber stoppers is very short. Merely the waiting time needed for probe ring-down and filter settling time is usually enough for the solids-signal the have died out. If the stoppers contain certain 'liquid' components, like some silicone-oil components, it might be necessary to add some extra waiting time.

The mechanisms that are outlined above include applications of moving ampules by a single row. It is possible, however, that the ampules or syringes are positioned in multiple rows of an array or matrix. By applying specific NMR techniques (such as application of gradient fields) it is possible to selectively measure weight or other properties of the materials contained in any specific ampule or syringe. This is especially valuable when measuring already multiply packed containers already in stock According to one embodiment, one way to determine the contents of products arranged in a matrix is to employ gradient fields. Because the resonance frequency in NMR is linearly proportional to the magnetic field strength, a gradient field causes products in different positions to respond in a different frequency band. When filtering out these bands and thereby selecting the sample being questioned, it is possible to determine the weight or other properties of the contents by determining the amplitude of the free induction decay (FID), as described above.

Incomplete Magnetisation Measurement Techniques

In the application of NMR techniques to determine characteristics of the contents of containers, such as vials, in a non-stationary manner, prior to the sample being in the measurement position the sample is moving through the magnetic field and is therefore being pre-magnetised (or pre-polarised). At the measurement position, the sample may be excited with an excitation pulse, for example a 90° pulse. This pulse causes the spins of the protons to precess in a plane, perpendicular to the main magnetic field. The relaxation process is dominated by dephasing of the spin precessions of the individual protons, and this free induction decay (FID) signal is measured. The amplitude of this signal is linearly proportional to the amount of protons in the sample, and therefore a sample calibration allows the method to be used as a measurement method, such as for weighing.

The process of polarization is a process with a typical time-constant, the T1 (spin-lattice constant). Generally NMR measurements can be taken when the pre-magnetization is complete. This stage is reached when taking approximately 5 times T1 as a magnetization period. For many pharmaceutical products, the T1 is of the order of 1 second. For completely magnetised NMR measurements, a pre-magnetization step of 5 seconds would be necessary.

In embodiments in which the method is applied to fast moving samples, the measurement is applied to incompletely magnetised samples and this measurement is accurate enough if the history (in terms of exposure to the magnetisation field) of every subsequent sample is identical, for example: the T1 influencing factors are known (via specific calibration) and can be incorporated into the measurement calculations (for example, temperature), and the speed of every subsequent sample does not vary, or is accurately known and can be compensated for.

Figure 11:
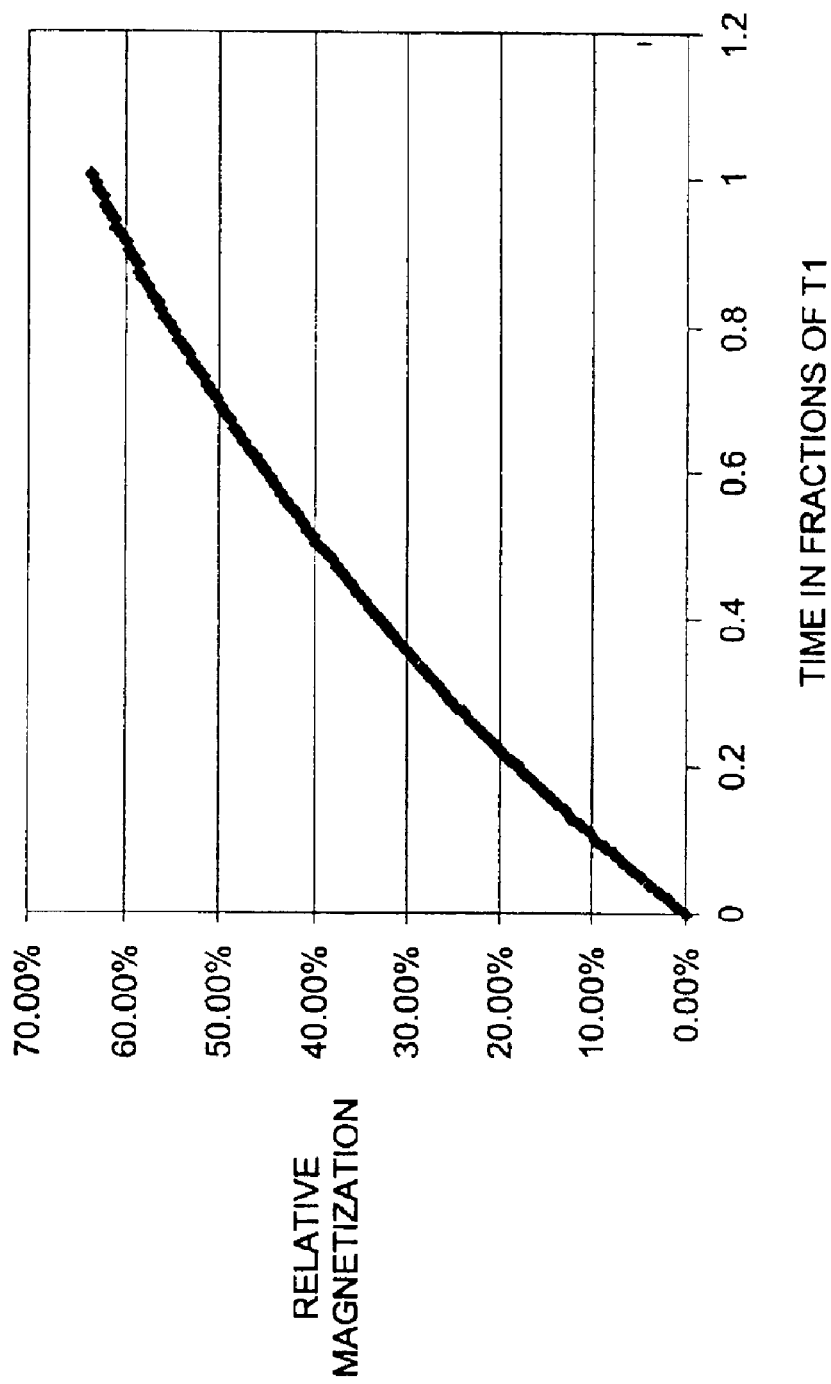
FIG. 11 is a graph showing a polarisation curve comparing relative magnetization to time in fractions of T1.

The graph of FIG. 11 shows a magnetisation curve and the consequence of having typically only half of a T1 available for magnetisation, yielding only 39% of magnetisation.

Although the invention has been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combined.

What is claimed is:

1. An improvement in a magnetic resonance method for determining at least one property of multiple samples in a filling or production line, comprising:

applying a magnetic field in a first direction in an interrogation zone for creating a net magnetisation within a sample located within the interrogation zone;

applying an alternating magnetic field in a second direction in the interrogation zone for temporarily changing the net magnetisation of the sample located within the interrogation zone; and monitoring energy emitted by the sample as the net magnetisation of the sample returns to its original state and generating an output signal having a characteristic which is proportional to the energy emitted;

characterised by:

introducing multiple samples into the interrogation zone simultaneously;

applying a gradient magnetic field to the interrogation zone wherein different positions within the interrogation zone are sensitive to different specific frequencies;

monitoring energy emitted by the samples in the different positions and generating an output signal having a characteristic which is proportional to the energy emitted corresponding thereto in different frequency bands; and, attributing the signals to specific positions and samples, and comparing the output signal characteristics of the specific positions and samples with like data obtained from at least one similar sample to provide an indication of the corresponding property of the samples.

2. The method of claim 1, including comparing the amplitude of the output signal and wherein the property indicated is the weight of the samples.

3. The method of claim 1, including comparing the shape of the output signal response curves and wherein the property indicated is the composition of the samples.

4. The method of any of claims 1, 2 or 3, wherein the multiple samples are contained within a blister pack.

5. The method of any of claims 1, 2 or 3, wherein the multiple samples are contained within separate containers arranged in a carrier.

6. The method of claim 5 wherein the carrier is a package for multiples of the containers.

7. The method of claim 5 wherein the carrier is a conveyor adapted to hold the containers.

8. The method of any of claims 1, 2 or 3 wherein the multiple samples are contained within containers having a component that is capable of influencing the magnetic field including at least one of:
 a. delaying said monitoring until the signal of the component dies out;
 b. including within the like data the signal corresponding to the component; or
 c. adapting the interrogation zone so as not to excite the component.

9. An improvement in a magnetic resonance method for determining at least one property of a sample in a filling or production line, wherein the sample is contained in a mechanically unstable container, comprising:

applying a magnetic field in a first direction in an interrogation zone for creating a net magnetisation within a sample located within the interrogation zone;

applying an alternating magnetic field in a second direction in the interrogation zone for temporarily changing the net magnetisation of the sample located within the interrogation zone; and monitoring energy emitted by the sample as the net magnetisation of the sample returns to its original state and generating an output signal having a characteristic which is proportional to the energy emitted;

characterised by:

inducing mechanical stability to the container for movement through the interrogation zone.

10. The method of claim 9 wherein the containers are selected from the group consisting of ampules, syringes, blister packs, blow-fill-seal packages, and bags.

11. The method of claim 9 or 10, wherein said inducing stability is selected from a method selected from the group consisting of:
 a. providing pockets to hold the containers, optionally including providing placing and removing means;
 b. guiding the containers in a scrolling helical transport structure;
 c. carrying the containers in an array, optionally in a cassette system;
 d. adapting a conveyor to hold the containers while being transported through the interrogation zone;
 e. feeding the containers through the interrogation zone without any inter-distance.

12. The method of claim 11 wherein multiple containers are introduced into the interrogation zone simultaneously, including one of:
 a. exciting and measuring one sample at a time; or
 b. applying gradient magnetic fields to separate containers by frequency band.

13. The method of claim 12 including:

introducing multiple samples into the interrogation zone simultaneously;

applying a gradient magnetic field to the interrogation zone wherein different positions within the interrogation zone are sensitive to different specific frequencies;

monitoring energy emitted by the samples in the different positions and generating an output signal having a characteristic which is proportional to the energy emitted corresponding thereto in different frequency bands; and, attributing the signals to specific positions and samples, and comparing the output signal characteristics of the specific positions and samples with like data obtained from at least one similar sample to provide an indication of the corresponding property of the samples.

14. The method of claim 9 or 10 wherein the container has a component that is capable of influencing the magnetic field including at least one of:
 a. delaying said monitoring until the signal of the component dies out;
 b. including within the like data the signal corresponding to the component; or
 c. adapting the interrogation zone so as not to excite the component.

15. The method of claim 1 or 9 wherein the energy emitted by the samples is monitored and the output signal is generated prior to the samples reaching complete magnetization at T1.

16. The method of claim 1 or 9 wherein the output signal characteristic is output signal amplitude.

* * * * *